US010982051B2

(12) United States Patent
Dussaud et al.

(10) Patent No.: US 10,982,051 B2
(45) Date of Patent: Apr. 20, 2021

(54) AQUEOUS COMPOSITIONS FOR HAIR TREATMENT COMPRISING POLYORGANOSILOXANES WITH POLYHYDROXYAROMATIC MOIETIES

(71) Applicant: Momentive Performance Materials Inc., Waterford, NY (US)

(72) Inventors: Anne Dussaud, Tarrytown, NY (US); Roland Wagner, Bonn (DE); Katharina Streicher, Leverkusen (DE); Christian Wenske, Solingen (DE)

(73) Assignee: Momentive Performance Materials Inc., Waterford, NY (US)

( * ) Notice: Subject to any disclaimer, the term of this patent is extended or adjusted under 35 U.S.C. 154(b) by 377 days.

(21) Appl. No.: 15/614,035

(22) Filed: Jun. 5, 2017

(65) Prior Publication Data
US 2018/0346653 A1 Dec. 6, 2018

(51) Int. Cl.
| | | |
|---|---|---|
| *C08G 77/20* | (2006.01) |
| *C08G 77/18* | (2006.01) |
| *C08G 77/26* | (2006.01) |
| *A61K 8/65* | (2006.01) |
| *C08G 77/30* | (2006.01) |
| *C08G 77/14* | (2006.01) |
| *A61K 8/893* | (2006.01) |
| *C08G 77/00* | (2006.01) |
| *A61Q 5/12* | (2006.01) |
| *A61Q 5/02* | (2006.01) |
| *C07C 211/62* | (2006.01) |
| *A61K 8/36* | (2006.01) |
| *C01G 49/00* | (2006.01) |
| *C01G 9/00* | (2006.01) |

(52) U.S. Cl.
CPC ............... *C08G 77/20* (2013.01); *A61K 8/65* (2013.01); *A61K 8/893* (2013.01); *A61Q 5/02* (2013.01); *A61Q 5/12* (2013.01); *C08G 77/14* (2013.01); *C08G 77/18* (2013.01); *C08G 77/26* (2013.01); *C08G 77/30* (2013.01); *C08G 77/70* (2013.01); *A61K 8/36* (2013.01); *A61K 2800/596* (2013.01); *C01G 9/00* (2013.01); *C01G 49/00* (2013.01); *C07C 211/62* (2013.01)

(58) Field of Classification Search
None
See application file for complete search history.

(56) References Cited

U.S. PATENT DOCUMENTS

| | | |
|---|---|---|
| 2,770,631 A | 11/1956 | Merker et al. |
| 3,297,735 A | 1/1967 | Simmler |
| 4,698,178 A | 10/1987 | Huttinger et al. |
| 4,833,225 A | 5/1989 | Schaefer et al. |
| 4,891,186 A | 1/1990 | Schaefer et al. |
| 5,098,979 A | 3/1992 | O'Lenick, Jr. |
| 5,153,294 A | 10/1992 | O'Lenick, Jr. |
| 5,166,297 A | 11/1992 | O'Lenick, Jr. |
| 5,270,426 A | 12/1993 | Sakuta et al. |
| 5,606,077 A | 2/1997 | Lersch et al. |
| 5,672,338 A | 9/1997 | Berthiaume |
| 5,679,619 A | 10/1997 | Morgan et al. |
| 5,686,547 A | 11/1997 | Nye |
| 5,935,560 A | 8/1999 | Seper et al. |
| 6,240,929 B1 | 6/2001 | Richard et al. |
| 6,544,499 B1 | 4/2003 | Glenn, Jr. et al. |
| 6,555,505 B1 | 4/2003 | King et al. |
| 6,730,766 B2 | 5/2004 | Schattenmann et al. |
| 7,041,767 B2 | 5/2006 | Lange et al. |
| 7,148,327 B2 | 12/2006 | Kelly et al. |
| 7,217,777 B2 | 5/2007 | Lange et al. |
| 7,329,707 B2 | 2/2008 | Sandner et al. |
| 7,563,856 B2 | 7/2009 | Lange et al. |
| 7,563,857 B2 | 7/2009 | Lange et al. |
| 7,728,069 B2 | 6/2010 | Keul et al. |
| 9,308,668 B2 | 4/2016 | Delis et al. |
| 2005/0255073 A1 | 11/2005 | Sockel et al. |
| 2006/0188456 A1 | 8/2006 | Ferenz et al. |
| 2007/0048235 A1 | 3/2007 | Harmalker et al. |
| 2007/0106045 A1 | 5/2007 | Lange et al. |
| 2008/0027202 A1 | 1/2008 | Ferenz et al. |
| 2008/0213208 A1 | 9/2008 | Moeller et al. |
| 2009/0000638 A1 | 1/2009 | Wood et al. |
| 2009/0062459 A1 | 3/2009 | Thum et al. |
| 2009/0076238 A1 | 3/2009 | Lange et al. |
| 2009/0165812 A1 | 7/2009 | Resnick et al. |
| 2009/0211593 A1 | 8/2009 | Coppola et al. |
| 2010/0266651 A1 | 10/2010 | Czech et al. |
| 2011/0033411 A1 | 2/2011 | Wagner et al. |
| 2011/0039948 A1 | 2/2011 | Lange et al. |
| 2012/0031420 A1 | 2/2012 | Gormley et al. |
| 2012/0289649 A1 | 11/2012 | Wagner et al. |
| 2013/0259820 A1 | 10/2013 | Snyder et al. |
| 2015/0011449 A1 | 1/2015 | Snyder et al. |

FOREIGN PATENT DOCUMENTS

| | | |
|---|---|---|
| DE | 19505892 C1 | 3/1996 |
| DE | 10036533 A1 | 9/2001 |

(Continued)

OTHER PUBLICATIONS

Written Opinion and International Search Report from PCT/US2018-035778 dated Aug. 6, 2018.

(Continued)

*Primary Examiner* — Robert A Wax
*Assistant Examiner* — Randeep Singh
(74) *Attorney, Agent, or Firm* — Joseph S. Ostroff

(57) ABSTRACT

This invention relates to aqueous compositions for hair treatment, comprising polyorganosiloxanes A) having di- and trihydroxy-substituted aromatic groups and at least one surfactant B) selected from cationic surfactants B1) and anionic surfactants B2) in a certain weight ratio of the surfactant B) to the polyorganosiloxane A), and said aqueous compositions having a certain pH. The invention further relates to hair treatment compositions, comprising said aqueous compositions and to hair treatment processes using said aqueous compositions or hair treatment compositions.

18 Claims, No Drawings

(56) References Cited

FOREIGN PATENT DOCUMENTS

| | | |
|---|---|---|
| DE | 10036522 A1 | 2/2002 |
| DE | 10036532 A1 | 2/2002 |
| DE | 10253152 A1 | 6/2004 |
| DE | 102004002208 A1 | 8/2005 |
| EP | 0282720 A3 | 2/1988 |
| EP | 0295780 A1 | 5/1988 |
| GB | 722822 | 2/1955 |
| GB | 1182939 | 3/1970 |
| WO | 9301791 A1 | 4/1993 |
| WO | WO9429324 A1 | 12/1994 |
| WO | 0210256 A1 | 2/2002 |
| WO | 0210257 A2 | 2/2002 |
| WO | 0210259 A1 | 2/2002 |
| WO | 2004069137 A2 | 8/2004 |
| WO | 2005058863 A1 | 6/2005 |
| WO | 2007053307 A1 | 5/2007 |
| WO | 2008002757 A1 | 1/2008 |
| WO | 2009035970 A1 | 3/2009 |
| WO | 2009042083 A2 | 4/2009 |
| WO | 2012027369 A2 | 3/2012 |
| WO | 2012038334 A1 | 3/2012 |
| WO | 2012143371 A1 | 10/2012 |
| WO | 2013148629 A1 | 10/2013 |
| WO | 2013148635 A1 | 10/2013 |
| WO | 2013148635 A2 | 10/2013 |
| WO | 2014111514 A1 | 7/2014 |
| WO | 2016046178 A1 | 3/2016 |

OTHER PUBLICATIONS

Rogers et al., Human Hair Keratin-Associated Proteins (KAPS), International Review of Cytology, 2006, 251: 209-263.

Puchtler et al., "On the chemistry of formaldehyde fixation and its effects on immunohistochemical reactions", 82 (1985), pp. 201-204.

Wagner et al., "Silicon-Modified Carbohydrate Surfactants I: Synthesis of Siloxanyl Moieties and Containing Straight-Chained Glycosides and Amides", Applied Organometallic Chemistry, 1996; 10: 421-435.

4. SOFW-Journal, 132, 12-2006, 30-32.

U.S. Appl. No. 15/613,988.

U.S. Appl. No. 15/613,892.

K. Khanbabaee, T. van Ree, Nat. Prod. Rep., 2001, 18, 641-649.

AQUEOUS COMPOSITIONS FOR HAIR TREATMENT COMPRISING POLYORGANOSILOXANES WITH POLYHYDROXYAROMATIC MOIETIES

FIELD OF THE INVENTION

This invention relates to aqueous compositions for hair treatment, comprising polyorganosiloxanes A) having di- and trihydroxy-substituted aromatic groups and at least one surfactant B) selected from cationic surfactants B1) and anionic surfactants B2) in a certain weight ratio of the surfactant B) to the polyorganosiloxane A), and said aqueous compositions having a certain pH. The invention further relates hair treatment compositions, comprising said aqueous compositions and to hair treatment processes using said aqueous compositions or hair treatment compositions.

BACKGROUND OF THE INVENTION

Hair generally can be straight, wavy, curly, kinky or twisted. A human hair includes three main morphological components, the cuticle (a thin, outer-most shell of several concentric layers), the cortex (the main body of the hair), and, in case of higher diameter hair, the medulla (a thin, central core). The cuticle and cortex provide the hair strand's mechanical properties, that is, its tendency to have a wave, curl, or kink. A straight hair strand can resemble a rod with a circular cross-section, a wavy hair strand can appear compressed into an oval cross-section, a curly strand can appear further compressed into an elongated ellipse cross-section, and a kinky hair strand cross-section can be flatter still.

The primary component of hair is the cross-linked, alpha-helix protein keratin. Keratins are intermediate filament proteins found specifically in epithelial cells, e.g. human skin and hair, wool, feathers, and nails. The α-helical type I and II keratin intermediate filament proteins (KIFs) with molecular weights around 45-60 kDa are embedded in an amorphous matrix of keratin-associated proteins (KAPs) with molecular weights between 20 to 30 kDa (M. A. Rogers, L. Langbein, S. Praetzel-Wunder, H. Winter, J. Schweizer, J. Int Rev Cytol. 2006; 251:209-6); both intra- and intermolecular disulfide bonds provided by cystines contribute to the cytoskeletal protein network maintaining the cellular scaffolding. In addition to the disulfide cross-links ionic bonding or salt bridges which pair various amino acids found in the hair proteins contribute to the hair strand's outward shape.

It is known in the art that hair can be treated with functionalized silicones which deliver one or more cosmetic benefits, such as conditioning, shine and UV protection as well as color retention. Typically, these silicones are physically deposited on the fiber surface (cuticle) and therefore responsible for the outward appearance of the hair. They can be removed partially or completely by repeated washing processes. While the deposited silicones considerably improve the surface properties of hair, i.e. smoothness and friction, they do not substantially impact the shape, the mechanical properties and the release properties of the hair. Alternative hair treatment methods are available, but these often involve the use of harsh and regulated substances. There has been a need for efficient compounds for the treatment of hair which can be synthesized in a straight forward and cost efficient way, which are easy to formulate and easy to use, yielding long term stable formulations even in the presence of other performance ingredients and which are useful for strengthening of hair, for hair color retention, for hair color enhancement, for hair color protection, for shaping of hair, i.e. the curling and straightening of hair, for hair conditioning, for hair smoothening or softening, for hair straightening, and for improving manageability of the hair, in particular for improving the combability of the hair. In particular, benefits regarding the retention of artificial hair colours without the usage of strongly irritating auxiliaries should be achieved.

WO2016046178 discloses polyhydroxyaromatic silicones for the treatment of hair. It does not disclose long term stable aqueous compositions that are easy to prepare and easy to use and where the polyhydroxyaromatic polyorganosiloxanes are stably dissolved even in the presence of other performance ingredients. Only this type of formulation guarantees a straight transport into the hair and a high crosslinking power.

Accordingly there was a need for long term stable, easy to prepare and easy to use compositions which are in addition robust towards the presence of other performance ingredients and which provide a hair strengthening benefit and a hair coloration benefit accompanied by a benefit on a silicone typical hair smoothness without the usage of strongly irritating auxiliaries.

The present inventors found that aqueous compositions for hair treatment, comprising polyorganosiloxanes A) having di- and trihydroxy-substituted aromatic groups and at least one surfactant B) selected from cationic surfactants B1) and anionic surfactants B2) in a certain weight ratio of the surfactant B) to the polyorganosiloxane A), and said aqueous compositions having a certain pH can be synthesized in a straightforward and cost-efficient way, are easy to formulate and to use, have long-term stability, and are useful for strengthening of hair, for hair coloring, for hair color retention, for hair color enhancement, for hair color protection, for shaping of hair, i.e. the curling and straightening of hair, for hair conditioning, for hair smoothening or softening, for hair straightening, and for improving manageability of the hair, in particular for improving the combability of the hair.

SUMMARY OF THE INVENTION

In accordance with the present invention, aqueous compositions for hair treatment are provided, comprising at least one polyorganosiloxane A) having an average number of 2 to 1000 siloxy units selected from the siloxy groups of the formulas:

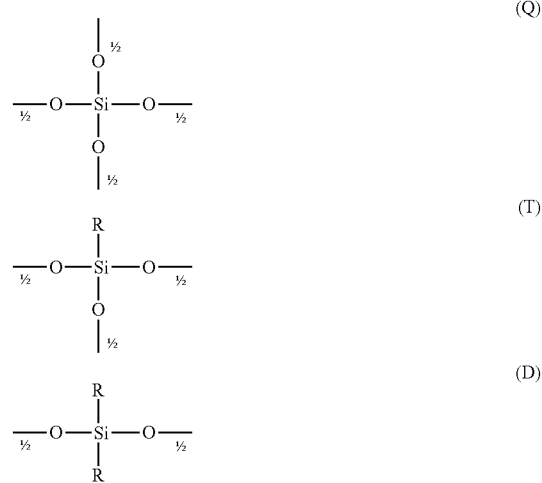

-continued

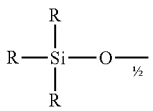
(M)

wherein
each R is independently selected from $R^1$ and at least one group $R^{F1}$, wherein
$R^1$ is selected from organic groups bound to the silicon atoms by a carbon atom, and two groups $R^1$ may form a bridging group between two silicone atoms, and
$R^{F1}$ is selected from organic groups different from $R^1$ and is bound to the silicon atoms by a carbon atom, which contain at least one functional group F1 selected from the group consisting of di- and trihydroxy-substituted aromatic groups, and
at least one surfactant B) selected from the group consisting of cationic surfactants B1) and anionic surfactants B2),
wherein the weight ratio of the surfactant B) to the polyorganosiloxane A) is at least 0.06, and wherein said aqueous composition has pH value at 20° C. of less than 7.5,
hair treatment compositions, comprising said aqueous compositions and hair treatment processes using said aqueous compositions or hair treatment compositions.

DETAILED DESCRIPTION OF THE INVENTION

Thus in a first aspect present invention an aqueous composition for hair treatment is provided, comprising at least one polyorganosiloxane A) having an average number of 2 to 1000 siloxy units selected from the siloxy groups of the formulas:

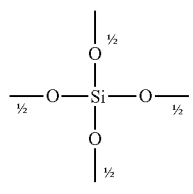
(Q)

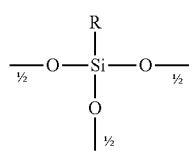
(T)

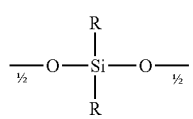
(D)

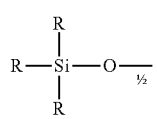
(M)

wherein
R is selected from $R^1$ and at least one group $R^{F1}$, wherein $R^1$ is selected from organic groups bound to the silicon atoms by a carbon atom, and two groups $R^1$ may form a bridging group between two silicone atoms, and
$R^{F1}$ is selected from organic groups different from $R^1$ and is bound to the silicon atoms by a carbon atom, which contain at least one functional group F1 selected from the group consisting of di- and trihydroxy-substituted aromatic groups, and
at least one surfactant B) selected from the group consisting of cationic surfactants B1) and anionic surfactants B2),
wherein the weight ratio of the surfactant B) to the polyorganosiloxane A) is at least 0.06, and
wherein said aqueous composition has pH value at 20° C. of less than 7.5.

Preferably the aqueous compositions according to the invention at 20° C. have a pH of less than 7, preferably less than 6, more preferably less than 5, and preferably more than 2.

Preferably the aqueous composition according to the invention shows no phase separation at 25° C. for at least 30 days, more preferably for at least 45 days, and even more preferred for at least 60 days.

The aqueous composition for hair treatment according to the invention comprises water, preferably in an amount of at least 1 weight-%, more preferably at least 5 weight-%, more preferably at least 10 weight-%, more preferably at least 15 weight-%, more preferably at least 20 weight-%, and preferably up to 95 weight-%, more preferably up to 90 weight-%, more preferably up to 85 weight-%, more preferably up to 80 weight-%, more preferably up to 75 weight-%, more preferably up to 70 weight-%, based on the total weight of the aqueous compositions.

In a preferred embodiment of the polyorganosiloxane A) of the invention the molar portion of the siloxanyl units which contain at least one radical $R^{F1}$ to all siloxanyl units of the polyorganosiloxane A) is 3.33 to 100 mol %, more preferred 5 to 100 mol %, even more preferred 5 to 50 mol %, most preferred 10 to 50 mol %.

In another preferred embodiment of the polyorganosiloxane A) of the invention the portion of branching T and Q moieties is 0 to 50%, preferred 0 to 20%, more preferred 0 to 10%, specifically 0 to 5%, more specifically 0% based on the number of all siloxy units.

The average number on siloxy units in the polyorganosiloxane A) according to the invention is 2 to 1000, preferred 2 to 300, more preferred 2 to 30, even more preferred 2 to 20, even more preferred 2 to 15. The average number on siloxy units can be determined i.e. by GPC (Gel Permeation Chromatography) using a system calibration versus polystyrene standards.

It is within the scope of the invention to use mixtures of different polyorganosiloxanes A) according to the invention.

Mixtures of polyorganosiloxanes yield e.g. bi-, tri- and higher modal distributions. Bimodal mixtures having a bimodal distribution are preferred. One preferred embodiment of the invention is a mixture comprising short chained siloxanes bearing on average 2 to 15 siloxy units and longer chained siloxanes bearing on average 16 to 30 siloxy units. A mixture of this composition has the advantage that depending on the size of the molecules different locations within the hair structure can be modified with silicone polymers.

In a further embodiment of the invention the polyorganosiloxanes A) in addition to $R^{F1}$ have at least one further functional organic group $RF^2$ different from $R^1$ and $RF^1$, which is bound to the silicon atoms by a carbon atom and which comprises at least one functional group F2, selected from:

alkoxy silyl group,
amino group, including azetidine group,
ammonium group, including azetidinium group,
phosphonium group,
epoxy group,
carbonate group,
urethane group,
isocyanate group, including blocked isocyanate group,
urea group,
amido group, including carbamoyl group

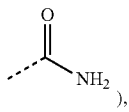

aldehyde group

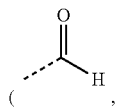

wherein the dotted line is a single bond)
methylol group
acetale or half acetale group,
Schiff-Base or enamine group,
zwitterionic group,
carboxylic acid or carboxylate group,
sulfonic acid or sulfonate group,
sulfuric acid half ester or sulfate group,
phosphoric acid ester or phosphate group,
phosphonic acid ester or phosphonate group,
phosphorous acid ester or phosphite group,
xanthogenate/xanthogenate ester group,
thiosulfato group,
a monohydroxy-substituted aromatic group,
mercapto group,
saccharide group,
polyether group with up to 60 carbon atoms,
thio ester,
thio ether group,
and combinations thereof.

In preferred embodiment of the invention the molar portion of the radicals $R^{F2}$ is 0 to 150 mol % based on the number of the radicals $R^{F1}$. If $R^{F2}$ is present the molar portion of the radicals $R^{F2}$ is preferably 30 to 100 mol % based on the number of the radicals $R^{F1}$.

The organic radicals $R^1$ are preferably selected from the a group consisting of straight-chain, cyclic or branched, saturated, unsaturated or aromatic hydrocarbon radicals which have up to 100 carbon atoms which optionally contain one or more groups selected from —O—, and which are optionally substituted by one more groups selected from the group consisting of hydroxyl, halogen (like chlorine, fluorine), a polyether radical with up to 60 carbon atoms, and/or
two radicals $R^1$ from different siloxy moieties form a group $R^3$ which is selected from divalent hydrocarbons radical which have up to 30 carbon atoms, and may contain optionally one or more groups selected from —O—, —NH—, —C(O)—, —C(S)—, tertiary amino groups

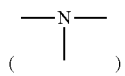

and quaternary ammonium groups

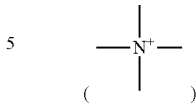

and wherein $R^3$ may optionally be substituted by one or more hydroxyl groups or halogen atoms, with the proviso that $R^3$ is bound to the silicon atoms via a carbon atom, more preferably $R^1$ is selected from the group consisting of n-, iso-, or tert.-$C_1$-$C_{22}$-alkyl, $C_2$-$C_{22}$-alkoxyalkyl, $C_5$-$C_{30}$-cycloalkyl, $C_5$-$C_{30}$-aryl, $C_5$-$C_{30}$-aryl($C_6$-$C_{30}$)alkyl, $C_6$-$C_{30}$-alkylaryl, $C_2$-$C_{22}$-alkenyl, $C_2$-$C_{22}$-alkenyloxyalkyl, which optionally can be each substituted by hydroxyl and halogen, and which optionally can contain one or more ether groups, and/or
$R^{F2}$ is selected from hydrocarbon radicals which have up to 100 carbon atoms and may contain one or more groups selected from —O—, —S—, —NR$^2$—, in which
$R^2$ is selected from the group consisting of hydrogen, a monovalent, straight-chain, cyclic or branched, saturated, unsaturated or aromatic hydrocarbon radical which has up to 60 carbon atoms and which may contain one or more groups selected from —O—, —S—, —NH—, —C(O)— and —C(S)—, and which may be substituted by one or two hydroxyl groups, and
which may optionally be substituted by one or more substituents selected from the group consisting of a hydroxyl group, an optionally substituted heterocyclic group preferably containing one or more nitrogen atoms, amino, alkylamino, dialkylamino, polyether radicals and polyetherester radicals, where, when a plurality of —NR$^2$— groups is present, they may be the same or different, and with the proviso that $R^{F2}$ contains at least one substituent group that comprises a functional group F2.

$R^2$ is preferably hydrogen, a monovalent, straight-chain, cyclic or branched, saturated, unsaturated or aromatic hydrocarbon radical which has up to 20 carbon atoms and may contain one or more groups selected from —O—, —NH—, —C(O)— and —C(S)—, and which may optionally be substituted by one or more substituents selected from the group consisting of a hydroxyl group, more preferred $R^2$ is hydrogen, a monovalent, straight-chain, cyclic or branched, saturated, unsaturated or aromatic hydrocarbon radical which has up to 10 carbon atoms and may contain one or more groups selected from —O—, —NH—, —C(O)— and —C(S)—, and which may optionally be substituted by one or more substituents selected from the group consisting of a hydroxyl group, preferably selected from hydrogen, methyl, ethyl, n-propyl, i-propyl, n-butyl, cyclohexyl, morpholinyl, oligo ethylene oxide, oligo propylene oxide, oligo ethylenepropylene oxides, oligo ethylene-propylene-butylene oxides, The organic radicals $R^1$ are more preferably selected from the a group consisting of n-, iso-, or tert. —$C_1$-$C_{22}$-alkyl, $C_2$-$C_{22}$-alkoxyalkyl, $C_5$-$C_{30}$-cycloalkyl, $C_6$-$C_{30}$-aryl, $C_6$-$C_{30}$-aryl($C_1$-$C_6$)alkyl, $C_6$-$C_{30}$-alkylaryl, $C_2$-$C_{22}$-alkenyl, $C_2$-$C_{22}$-alkenyloxyalkyl, which can be substituted by one or more, preferred up to five, groups selected from hydroxyl and halogen, preferred fluorine, and can contain one or more ether groups, in particular, $R^1$ can be selected from $H_3C$—, $CH_3CH_2$—, $CH_3CH_2CH_2$—, $(CH_3)_2CH$—, $C_8H_{17}$— and $C_{10}H_{21}$—, $H_2C=CH$—O—$(CH_2)_{1-6}$, cycloaliphatic radicals, i.e. cyclohexylethyl, limonyl, norbomenyl, phenyl, tolyl, xylyl, benzyl and 2-phenylethyl, halogen($C_1$-$C_{10}$)alkyl, i.e. $C_fF_{fn+1}CH_2CH_2$— wherein f is 1 to 8, e.g. $CF_3CH_2CH_2$—, $C_4F_9CH_2CH_2$—, $C_6F_{13}CH_2CH_2$—, $C_2F_5$—$O(CF_2$—$CF_2$—$O)_{1-10}CF_2$—, $F[CF(CF_3)$—$CF_2$—$O]_{1-5}$—$(CF_2)_{0-2}$—, $C_3F_7$—$OCF(CF_3)$— and $C_3F_7$—$OCF(CF_3)$—$CF_2$—$OCF(CF_3)$—, more preferably $R^1$ is methyl, vinyl, phenyl, 3,3,3-trifluoropropyl, most preferred methyl.

In a preferred embodiment of the invention $R^{F1}$ has the structure:

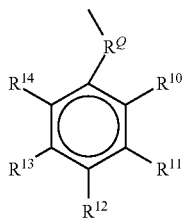

wherein
$R^9$ is selected from $R^3$ as defined above, with the additional possibility that $R^3$ is substituted by nitrogen containing groups, such as —$NH_2$, —$NHR^2$, —$N(R^2)_2$, wherein $R^2$ is as defined above,
$R^{10}$, $R^{11}$, $R^{12}$, $R^{13}$, $R^{14}$ are the same or different from each other and are selected from hydroxyl and $R^2$, as defined above, with the proviso that 2 to 3 groups $R^{10}$ to $R^{14}$, more preferred 2 or 3 groups are hydroxyl (—OH).

The groups F2 are preferably selected from:
amino groups, including azetidine group of the following formula

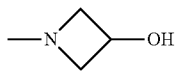

amido groups, including carbamoyl,
ammonium group, including azetidinium group of the following formula

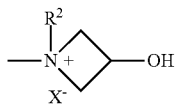

wherein $R^2$ is as defined above, and $X^-$ is halogenide, preferably chloride, bromide, iodide, more preferred chloride,
epoxy group,
aldehyde group,
carbonate group,
isocyanate group, especially blocked isocyanate group,
xanthogenate/xanthogenate ester group,
alkoxy silyl group
thiosulfato group,
wherein each of the aforementioned groups F2 are preferably bound via a group $R^3$ to the silicon atom, wherein $R^3$ is as defined above, that is $R^{F2}$ is $R^3$ substituted by at least one group F2.

The groups $R^{F2}$ are preferably selected from the group consisting of:
quaternary phosphonium containing radicals of the formula

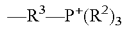

wherein
$R^3$ is as defined above and is bound to silicon and phosphorus by a carbon atom, the radicals
$R^2$ are as defined above, and can be identical or different and preferably at least one radical $R^2$ is not hydrogen,
phosphine group containing radicals of the formula,

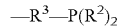

wherein
$R^3$ as defined above and is bound to silicon and phosphorus by a carbon atom, the radicals $R^2$ are as defined above, and can be identical or different and preferably at least one radical $R^2$ is not hydrogen,
epoxy groups containing radicals selected from:

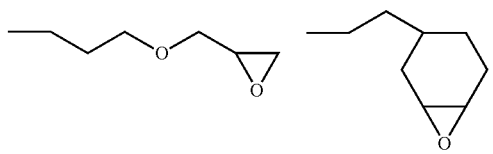

carbonate groups containing radicals selected from:

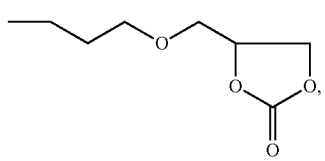

urethane groups containing radicals selected from:

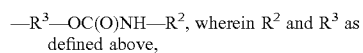

urea groups containing radicals selected from:

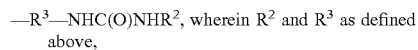

amide groups containing radicals selected from:

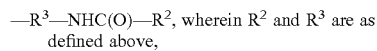

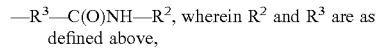

enamine groups containing radicals selected from:

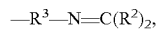

wherein $R^2$ are identical or different (but not hydrogen) and $R^2$ and $R^3$ are as defined above, preferably synthesized from amino functional polyorganosiloxanes and ketones, preferred aliphatic and aromatic ketones with up to 14 carbon atoms, more preferred aliphatic C3-C14 ketones, aromatic C8 to C12 ketones,
enamine groups containing radicals selected from:

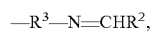

wherein $R^2$ and $R^3$ are as defined above, but $R^2$ is not hydrogen, preferably synthesized from amino functional polyorganosiloxanes and monoaldehydes, preferred aliphatic and aromatic aldehydes with up to 14 carbon atoms, more preferred aliphatic C1-C14 aldehydes, aromatic C7 to C11 aldehydes,
aldehyde groups containing radicals selected from:

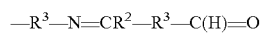

wherein $R^3$ are identical or different and $R^2$ and $R^3$ are as defined above, preferably synthesized from amino functional polyorganosiloxanes which are reacted with dialdehydes, i.e. glyoxal, malonic dialdehyde, succinic dialdehyde, phthalic dialdehyde, isophthalic dialdehyde, terephthalic dialdehyde, methylol groups comprising moieties of the formulas

—R³—O—CH₂OH,

—R³—N(R²)(CH₂OH),

—R³—N(R²)₂(CH₂OH),

—R³—N(CH₂OH)₂

—R³—N⁺(R²)(CH₂OH)₂

—R³—C(O)—NH—CH₂OH

—R³—C(O)—N(CH₂OH)₂ wherein R² and R³ are as defined above, and preferably R³ comprises a moiety of the formula:

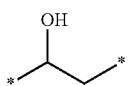

(wherein each * denotes a bond), which is preferably formed by the ring opening reaction of an epoxide or carbonate group, which are preferably selected from:

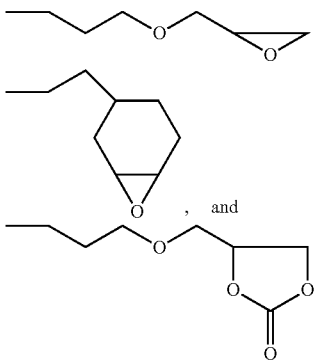

which groups are bound to the silicon atom of a siloxy group from the left side, zwitterionic groups containing radicals selected from:
carbobetaine groups containing radicals:

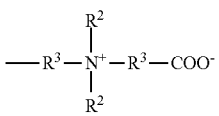

or their neutral form:

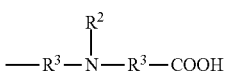

and salts thereof, wherein R² and R³ are identical or different and R² and R³ are as defined above, sulphobetaine groups containing radicals:

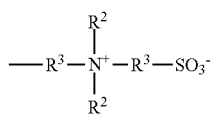

or their neutral form:

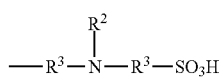

and salts thereof, wherein R² and R³ are identical or different and R² and R³ are as defined above, carboxylic acid or carboxylate groups containing radicals selected from:

—R³—COOR², —R³—COO⁻ wherein R² and R³ are as defined above, sulfonic acid or sulphonate groups containing radicals selected from:

—R³—SO₃R², —R³—SO₃⁻ wherein R² and R³ are as defined above, sulfuric acid half ester/sulfate groups containing radicals selected from:

—R³—OSO₃R², —R³—OSO₃⁻ wherein R² and R³ are as defined above, phosphoric acid ester/l phosphate groups containing radicals selected from:

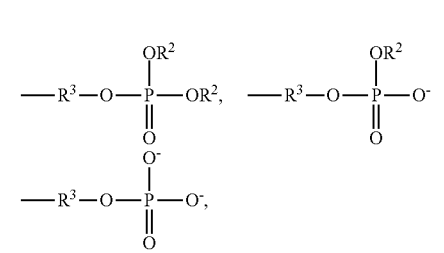

wherein R² and R³ are as defined above, fluoro phosphoric acid ester groups containing radicals selected from:

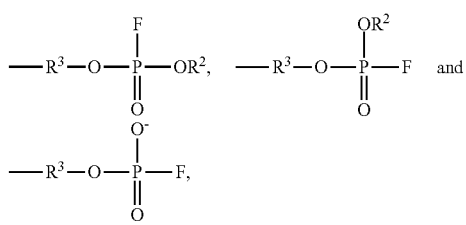

wherein R² and R³ are as defined above, phosphonic acid ester/phosphonate groups containing radicals selected from:

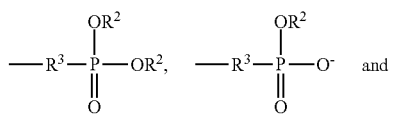

-continued

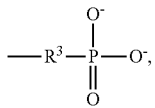

and their protonated forms,
wherein $R^2$ and $R^3$ as defined above and with $R^3$ linked by a carbon atom to a phosphorus atom,
  phosphorous acid ester/phosphite groups containing radicals selected from:

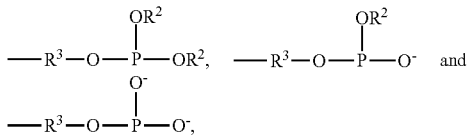

wherein $R^2$ and $R^3$ as defined above and linked by a carbon atom to the oxygen atom of the phosphorous acid ester/phosphite group,
  xanthogenate/xanthogenate ester groups containing radicals selected from:

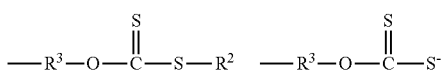

wherein $R^2$ and $R^3$ as defined above,
and wherein the cations neutralizing anionic functional groups are selected from:
ammonium groups ($N^+(R^2)_4$, wherein $R^2$ as defined above,
phosphonium groups ($P^+(R^2)_4$, wherein $R^2$ as defined above,
as well as one to trivalent metal cations,
and wherein the anions neutralizing the cationic functional groups are selected from: halogenide, hydroxide, borate, sulfate, phosphate, nitrate and carboxylate.

The polyorganosiloxanes A) are preferably selected from the formulas:

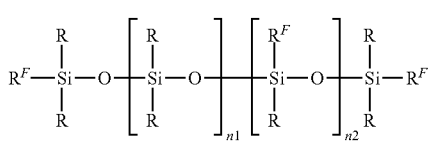

(IIIa)

wherein
R is $R^1$, and $R^F$ is selected from $R^{F1}$ and $R^{F2}$, preferably $R^{F1}$, each as defined above, with the proviso that at least one $R^F$ is $R^{F1}$, and the sum of the average numbers n1+n2 is 0 to 28, preferred 0 to 25, more preferred 0 to 20, even more preferred 5 to 15,

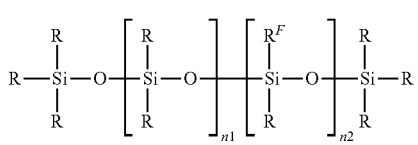

(IIIb)

wherein
R is $R^1$, and $R^F$ is selected from $R^{F1}$ and $R^{F2}$, preferably $R^{F1}$, each as defined above, with the proviso that at least one $R^F$ is $R^{F1}$, and the sum of the average numbers n1+n2 is 1 to 28, preferred 1 to 25, more preferred 1 to 20, even more preferred 5 to 15, with n2≥1, preferred 1 to 28, more preferred 1 to 10, even more preferred 1 to 5, with n2≥1, and

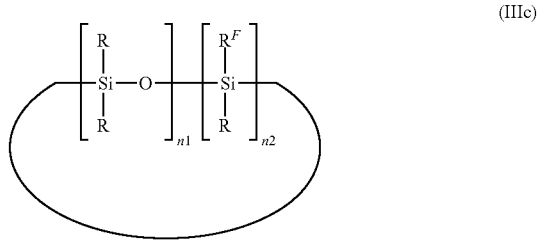

(IIIc)

R is $R^1$, and $R^F$ is selected from $R^{F1}$ and $R^{F2}$, preferably $R^{F1}$, each as defined above, with the proviso that at least one $R^F$ is $R^{F1}$, and wherein the sum of the average numbers n1+n2 is 3 to 7 with n2≥1, more preferred 3 to 5.

in the above polysiloxane formulas the siloxy units having indices n1 and n2 can be arranged in any order, such as regular alternatingly arranged units, periodically arranged units, statistically arranged units and blockwise arranged units, preferably they are statistically arranged.

Preferably the di- or trihydroxy-substituted aromatic groups are di- or trihydroxy-substituted phenyl groups which may optionally contain further substituents such as a C1-C6 alkyl group, in particular a methyl group or C1-C6 alkoxy groups such as methoxy.

Preferably the di-, trihydroxy-substituted aromatic groups have the structure:

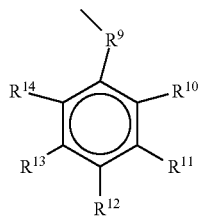

wherein
$R^9$=$R^3$ as defined above with an additional possibility of a substitution by nitrogen containing groups, preferred —$NH_2$, —$NHR^2$, —$N(R^2)_2$, therein $R^2$ is as defined above. $R^{10}$, $R^{11}$, $R^{12}$, $R^{13}$, $R^{14}$=$R^2$ as defined above with the proviso that 2 to 3 groups $R^{10}$ to $R^{14}$, are hydroxyl (—OH), preferably derived from allyl derivatives, 1-allyl-3,4-dihydroxybenzene, 1-allyl-2,6-dihydroxybenzene and dihydroxy benzoic acids or their partial esters, i.e. 2,3-dihydroxy benzoic acid, 2,4-dihydroxy benzoic acid, 2,5-dihydroxy benzoic acid, 2,6-dihydroxy benzoic acid, 3,4-dihydroxy benzoic acid, 3,5-dihydroxy benzoic acid, dihydroxy cinnamic acids or their partial esters, i.e. 3,4-dihydroxy cinnamic acid, trihydroxy benzoic acids or their partial esters, i.e. 2,3,4-trihydroxy benzoic acid, 2,3,5-trihydroxy benzoic acid, 2,3,6-trihydroxy benzoic acid, 2,4,5-trihydroxy benzoic acid, 2,4,6-trihydroxy benzoic acid, 3,4,5-trihydroxy benzoic acid, trihydroxy cinnamic acids or their partial esters, i.e. 3,4,5-dihydroxy cinnamic acid.

In a particular preferred embodiment di- or trihydroxy-substituted aromatic acids, in particular, di- or trihydroxy-substituted benzoic acids are reacted with epoxy-functional polyorganosiloxanes to form ester functional linking groups which are bound to the silicon atom and which carry the di- or trihydroxy-substituted aromatic groups, in particular the di- or trihydroxy-substituted phenyl groups.

In such a preferred embodiment the group $R^3$ results preferably from the reaction of epoxy-modified silicones with di- or trihydroxy-substituted aromatic acids, in particular di- or trihydroxy-substituted benzoic acids. Most preferred Si—H functional silicones are reacted with allyl glycidyl ether in a hydrosilylation reaction, and the resulting epoxy siloxane moiety of formula:

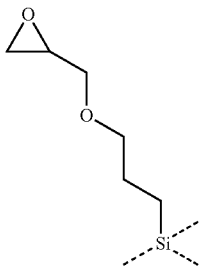

(dotted lines are free valencies of the silicon atom)
is reacted with an hydroxy benzoic acids to form $R^{F1}$ being —$R^3$—$F^1$ being a group of the formula:

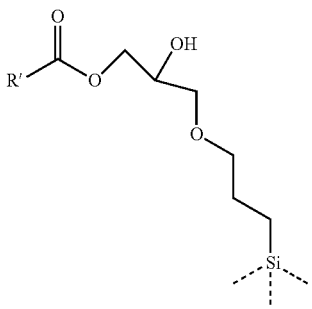

(dotted lines are free valencies of the silicon atom) with $R^1$ being a di- or trihydroxyl-substituted aromatic group, preferably a di- or trihydroxy-substituted phenyl group, most preferred a 3,4-dihydroxy phenyl and 3,4,5-trihydroxy phenyl group.

So most preferred the group $R^{F1}$ is derived from di- or trihydroxy benzoic acids, in particular, 3,4-dihydroxy benzoic acid and 3,4,5-trihydroxy benzoic acid.

Details on the incorporation of the radicals $R^{F2}$ containing the groups F2 are described e.g. in WO 2012/143371 or WO 2016/046178.

In a preferred embodiment the polyorganosiloxanes according to the invention contain at least one radical of the formula $M^F$:

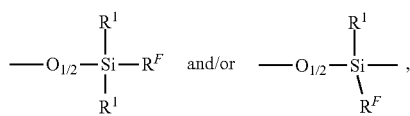

wherein $R^1$ is as defined above, and $R^F$ is selected from $R^{F1}$ and $R^{F2}$, preferably $R^{F1}$, each as defined above, with the proviso that at least one $R^F$ is $R^{F1}$.

In a preferred embodiment of the invention more than one type of polyorganosiloxanes according to the invention is used simultaneously.

Particularly preferred polysiloxanes A) include polysiloxanes selected from the group consisting of the following formulas:

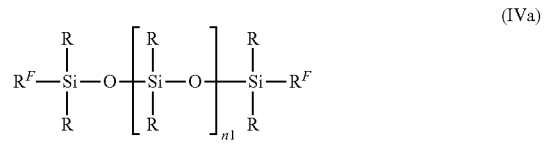

(IVa)

wherein
R is alkyl, preferably methyl, n1 is 0 to 20, preferably 1 to 10,
$R^F$ is —$R^3$—F1, wherein $R^3$ and F1 are as defined above, preferably —$R^3$—F1 is a group of the formula:

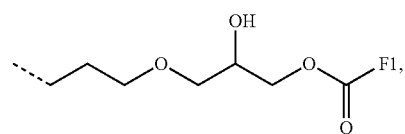

wherein F1 is as defined above, and the dotted line represents a single bond to the silicon atom, and preferably F1 is a group of formula:

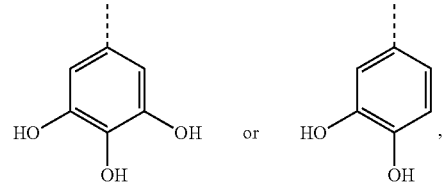

and preferably F1 is the group:

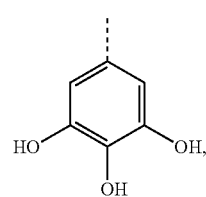

wherein in each formula the dotted line represents a single bond,

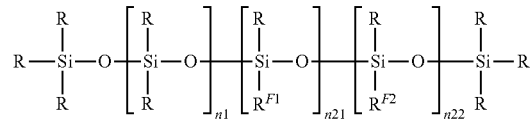

(IVb)

wherein
R is alkyl, preferably methyl,
n1 is 0 to 30, preferably 1 to 20,
n21 is 1 to 10, preferably 2 to 6,
n22 is 1 to 10, preferably 2 to 6,
$R^{F1}$ is —$R^3$—F1, wherein $R^3$ and F1 are as defined above, and preferably —R³—F1 is a group of the formula:

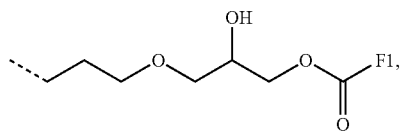

wherein F1 is as defined above, the dotted line represents a single bond to the silicon atom, and preferably F1 is a group of formula:

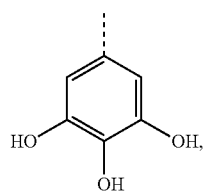

and preferably F1 is the group:

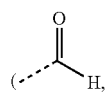

wherein in each formula the dotted line represents a single bond,
R$^{F2}$ is —R³—F2, wherein R³ and F2 are as defined above, and
preferably —R³—F2 is a group of the formula:

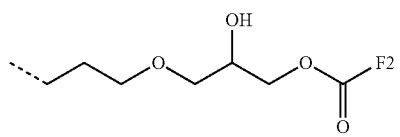

wherein F2 is as defined above, the dotted line represents a single bond to the silicon atom, and
preferably F2 is an aldehyde group

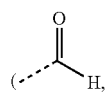

wherein the dotted line is a single bond), or
—R³—F2 is a group of the formula:

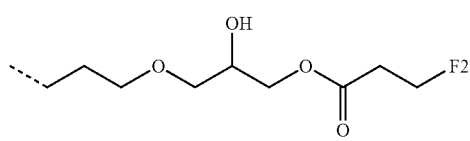

wherein F2 is as defined above and preferably F2 is an amido group, preferably a carbamoyl group

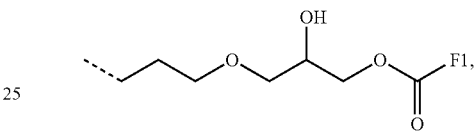

and

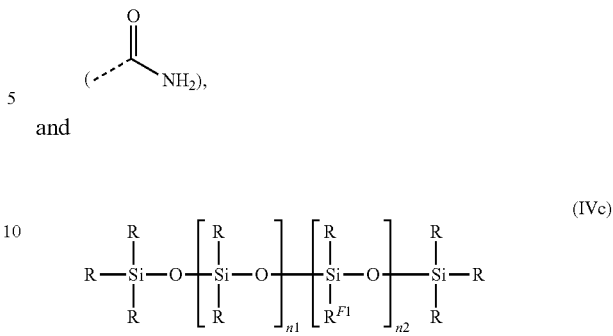

wherein
R is alkyl, preferably methyl, n1 is 0 to 20, preferably 1 to 10, n2 is 1 to 20, preferably 1 to 10,
R$^{F1}$ is —R³—F1, wherein R³ and F1 are as defined above,
preferably —R³—F1 is a group of the formula:

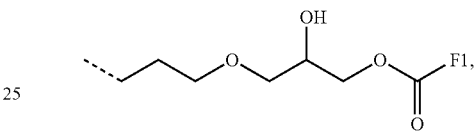

wherein F1 is as defined above, and the dotted line represents a single bond to the silicon atom, and preferably F1 is a group of formula:

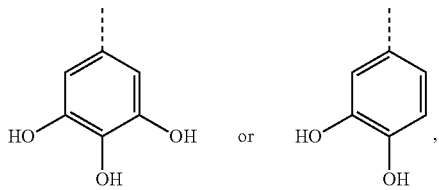

and preferably F1 is the group:

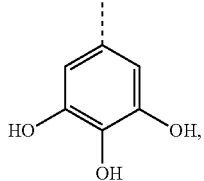

wherein in each formula the dotted line represents a single bond, and
wherein in the above polysiloxane formulas the siloxy units having indices n1, n21 and n22 can be arranged in any order, such as regular alternatingly arranged units, periodically arranged units, statistically arranged units and blockwise arranged units, preferably the siloxy units are arranged statistically.

In the aqueous compositions according to the invention, preferably the polyorganosiloxanes A) have number average molecular weights Mn<2000 g/mol, preferred<1500 g/mol, more preferred<1000 g/mol, as determined by GPC using polystyrene as standard.

It is possible to combine the polyorganosiloxanes A) according to the invention with other functional polyorganosiloxanes having e.g. functional group selected from amino, quaternary ammonium, and quaternary phosphonium groups alone or optionally in combination with anionic polyorganosiloxane compounds having functional group selected from carboxylic acid/carboxylate, sulphonic acid/sulphonate, sulfuric acid half ester/sulphate, phosphoric acid ester/phosphate, phosphonic acid ester/phosphonate, phosphorous acid ester/phosphite, and xanthogenate/xanthogenate ester. Examples for the above mentioned compounds are described in WO 2012/143371. It is preferred to combine the polyorganosiloxanes according to the invention with betaine functional polyorganosiloxanes. Examples for these compounds are described in WO 2012/143371. It is further preferred to combine the polyorganosiloxanes according to the invention with di- and polycationic compounds of the ABA or block copolymer type. Examples for these compounds are described in WO 02/10257, WO 02/10259 and DE 10036553.

Preferred precursors and intermediates are SiH functional, epoxy functional and carbonate functional polyorganosiloxanes. The preparation of Si-functional polyorganosiloxanes is described in the prior art (Silicone, Chemie und Technologie, Vulkan Verlag Essen 1989, S. 4). In one embodiment of the invention these SiH functional polyorganosiloxanes are reacted with olefinically or acetylenically unsaturated hydroxyaromatic compounds yielding the target molecules by hydrosilylation.

The preparation of epoxy functional polyorganosiloxane intermediates is described in the prior art (Silicone, Chemie und Technologie, Vulkan Verlag Essen 1989, S. 90). Preferred unsaturated epoxy precursors are allyl glycidyl ether, propargyl glycidyl ether and vinyl cyclohexene oxide. Preferably, these epoxy intermediates are reacted with amino, carboxylic acid or thiol functional precursors yielding the different target compounds.

In a preferred embodiment of the invention epoxy functional intermediates are reacted simultaneously or sequentially with precursors which introduce the radicals $R^{F1}$ and optionally $R^{F2}$.

The preparation of carbonate functional polyorganosiloxanes intermediates is described in the prior art. They can be synthesized from SiH functionalized polyorganosiloxanes and unsaturated carbonate precursors, i.e. allyl carbonate (U.S. Pat. Nos. 5,672,338, 5,686,547). Alternatively, they can be prepared from epoxy functionalized precursors by $CO_2$ insertion (DE 19505892) or by reaction of aminosiloxanes or aminosilanes with bifunctional carbonate coupling agents (WO 2005/058863). Preferably, these carbonate intermediates are reacted with amino functional precursors yielding the different target compounds.

Preferred hydrocarbon based precursors for the incorporation of hydroxyaromatic radicals $R^{F1}$ are olefinically or acetylenically unsaturated derivatives such as 1-allyl-3,4-dihydroxybenzene, 1-allyl-2,6-dihydroxybenzene. These hydrocarbon based precursors can be used in hydrosilylations with SiH functionalized polyorganosiloxanes. Other preferred hydrocarbon based precursors for the incorporation of hydroxyaromatic radicals $R^{F1}$ contain carboxylic acid or amino groups. Preferred examples for carboxylic acid functionalized precursors are hydroxy benzoic acids such as dihydroxy benzoic acids, e.g. 2,3-dihydroxy benzoic acid, 2,4-dihydroxy benzoic acid, 2,5-dihydroxy benzoic acid, 2,6-dihydroxy benzoic acid, 3,4-dihydroxy benzoic acid, 3,5-dihydroxy benzoic acid, trihydroxy benzoic acids, e.g. 2,3,4-trihydroxy benzoic acid, 2,3,5-trihydroxy benzoic acid, 2,3,6-trihydroxy benzoic acid, 2,4,5-trihydroxy benzoic acid, 2,4,6-trihydroxy benzoic acid, 3,4,5-trihydroxy benzoic acid.

Other preferred examples for carboxylic acid functionalized precursors are dihydroxy cinnamic acids or their partial esters, i.e. 3,4-dihydroxy cinnamic acid, trihydroxy cinnamic acids or their partial esters, i.e. 3,4,5-dihydroxy cinnamic acid.

In a preferred embodiment of the invention these carboxylic acid functionalized hydrocarbon precursors are reacted with epoxy functionalized polyorganosiloxane intermediates. Optionally, a catalyst, for example a tertiary amine, i.e triethylamine, is used (US 2012/0289649, example 1).

A preferred amino group containing precursors is for example 3,4-dihydroxyphenylethylamine or 3,4,5-trihydroxyphenylethylamine. Preferably, they are reacted with epoxy or carbonate functionalized polyorganosiloxane (DE 4318536, example 9; US 2011/0033411, example 4).

An example for carboxylic acid groups and amino groups containing precursors is 3,4,5-trihydroxyphenylalanine.

Primary and secondary amino groups containing polyorganosiloxanes as precursors are described in the prior art. Preferably, they can be synthesized from SiH functionalized polyorganosiloxane or silane precursors and unsaturated amines, for example allylamine, N-methyl-allylamine, hex-1-en-ylamine by hydrosilylation (R. Wagner et. al. Appl. Organomet. Chem., 1996, 10, 424). Alternatively, they can be synthesized from epoxy functionalized polyorganosiloxane and silane precursors by reaction with ammonia or primary amino functions containing amines (DE 4318536, example 9). Examples for primary amino functions containing amines are methylamine, ethylamine, n-propylamine, i-propylamine, polyether based monoamino derivatives, for example EO/PO based M-Jeffamines (Huntsman Corp.), glucamine, aminoethylmorpholine, ethylene diamine, 1,2-propylene diamine, 1,3-propylenediamine, aminoethylethanolamine, aminoethylpiperazine.

Amide groups containing polyorganosiloxanes can be synthesized e.g. from epoxy functional polyorganosiloxanes and difunctional precursors bearing carboxylic acid as well as amide moieties by esterification. An example is succinic acid monoamide, $HOOC-CH_2CH_2-C(O)NH_2$.

Further methods of introducing functional groups $R^{F2}$ are described in WO2016046178_A1.

In the aqueous compositions according to the invention the weight ratio of the surfactant B) to the polyorganosiloxane A) is preferably 0.06 to 12.

The aqueous compositions according to the invention preferably comprise 0.01 to 40 wt-% of the polyorganosiloxane A) based on the total weight of the aqueous composition.

Basically according to the invention one can distinguish between a more concentrated aqueous composition having higher concentrations of the polyorganosiloxanes A) which is used to prepare the more specific hair treating compositions comprising the polyorganosiloxanes A) in lower concentrations. However, also the more concentrated aqueous composition can be used directly as hair treatment compositions.

Suitable concentrations of the polyorganosiloxanes A) in more concentrated aqueous compositions according to the invention are e.g. 5 to 40 wt-%, preferably 7 to 20 wt-% based on the total weight of the aqueous composition.

In a preferred embodiment the aqueous compositions comprise 0.01 to 7 wt-% of the polyorganosiloxane A) based on the total weight of the aqueous composition. Such concentrations are particular suitable for direct use as hair treatment compositions.

In a preferred embodiment the aqueous compositions comprise 0.01 to 30 wt-%, more preferably 0.01 to 20 wt-% of the surfactant B) selected from B1) and B2) based on the total weight of the aqueous composition. (It should be noted that the weight percentages/weight ratios of the surfactant B) in the present application only refer to the amount of the cationic and anionic surfactants B1) and B2. That is, the amount given for the surfactants B) does not include other surfactants as described below).

In the case where the surfactant B) is a cationic surfactant B1) the weight ratio of the cationic surfactant B1) to the polyorganosiloxane A) is preferably 0.1 to 5, more preferably 0.5 to 4, even more preferably 1 to 3.

In the case where the surfactant B) is an anionic surfactant B2) the weight ratio of the anionic surfactant B2) to the polyorganosiloxane A) is preferably 0.1 to 15, more preferably 2 to 13, still more preferably 3 to 11.5.

In a preferred embodiment the aqueous composition according to the invention comprises at least one non-aqueous diluent or solvent C), preferably as described below. Preferably the ratio of the non-aqueous diluent C) to the polyorganosiloxane A) is at least 0.5, preferably at least 1.

In a preferred embodiment the aqueous composition according to the invention comprises less than 30% (wt/wt) of the non-aqueous diluent C), based on the total weight of the composition.

In the aqueous composition according to the present invention the cationic surfactant B1) is preferably selected from primary, secondary, or tertiary amine compounds having up to 50 carbon atoms and salts thereof, amido amine compounds having up to 50 carbon atoms and salts thereof, such as behenamidopropyl dimethylamine and quaternary ammonium compounds, having up to 50 carbon atoms, and preferably with up to 20 carbon atoms in the alkyl groups thereof, such as tetraalkyl ammonium compounds, e.g. hexadecyl-trimethylammonium salts, dimethyldioctadecylammonium salts, distearyldimethylammonium salts, cetrimonium salts, cetylpyridinium salts, alkylbenzyldimethylammonium salts such as benzalkonium salts, benzethonium salts, ester quats having at least one quaternary ammonium group and at least one ester group.

Preferred examples for cationic emulsifiers are quaternary ammonium compounds or amino compounds containing linear or branched C8 to C50, preferred C8 to 40, more preferred C8 to C30 organic groups which optionally have further functional groups, such as alkyl, fatty alcohol and fatty acid based emulsifiers, e.g. fatty acid based ester quats containing one or two fatty acid moieties, fatty amines and ethoxylated/propoxylated fatty amines, such as fatty alcohol polyoxyethylene ether ammonium sulfates.

Preferably, the cationic surfactant is a mono-long alkyl-tri short alkyl quaternized ammonium salt or di-long alkyl-di short alkyl quaternized ammonium salt wherein one or two alkyl substituents are independently selected from an optionally substituted alkyl group of from 9 to 30 carbon atoms and the other short alkyl groups are independently selected from an optionally substituted alkyl group of from about 1 to about 8 carbon atoms. In these cationic surfactants the long alkyl groups may be also replaced by an aromatic group, alkoxy group, polyoxyalkylene group, alkylamido group, hydroxyalkyl group, or alkylaryl group having up 9 to about 30 carbon atoms or the short alkyl groups are replaced by an aromatic group, alkoxy group, polyoxyalkylene group, alkylamido group, hydroxyalkyl group, alkylaryl group having up to about 8 carbon atoms.

Counter ions of the ammonium compounds (which may be quaternized ammonium compounds or protonated amino compounds) include salt-forming anions such as those selected from halogen, (e.g., chloride, bromide), acetate, citrate, lactate, glycolate, phosphate, nitrate, sulfonate, sulfate, alkylsulfate, glutamate, and alkyl sulfonate radicals.

The aliphatic groups in the cationic emulsifiers can contain, in addition to carbon and hydrogen atoms, ether linkages, and other groups such as amino groups. The longer chain aliphatic groups, e.g., those of about 9 carbons, or higher, can be saturated or unsaturated.

Preferably, one alkyl group is selected from an alkyl group of from about 9 to about 30 carbon atoms, more preferably from about 14 to about 26 carbon atoms, still more preferably from about 14 to 22 carbon atoms; the other alkyl groups are independently selected from the group consisting of —$CH_3$, —$C_2H_5$, —$C_2H_4OH$, —$CH_2C_6H_5$, and mixtures thereof; and the counter ion is selected from the group consisting of $Cl^-$, $Br^-$, $CH_3OSO_3^-$, and mixtures thereof.

Nonlimiting examples of such mono-long alkyl quaternized ammonium salt cationic surfactants include: behenyl trimethyl ammonium chloride available, for example, with tradename Genamine KDMP from Clariant, with tradename INCROQUAT TMC-80 from Croda and ECONOL TM22 from Sanyo Kasei; stearyl trimethyl ammonium chloride available, for example, with tradename CA-2450 from Nikko Chemicals; cetyl trimethyl ammonium chloride available, for example, with tradename CA-2350 from Nikko Chemicals; behenyttrimethylammonium methyl sulfate, available from FeiXiang; hydrogenated tallow alkyl trimethyl ammonium chloride; stearyl dimethyl benzyl ammonium chloride; and stearoyl amidopropyl dimethyl benzyl ammonium chloride. Cationic surfactants can amido amine surfactants such as stearamidopropyl dimethylamine, behenamidopropyl dimethylamine. Other preferred cationic surfactants are esterquat, for example dipalmitoylethyl hydroxyethylmonium methosulfate (for example tradename stepanquat GA90) or methyl bis [ethyltallowate]-2-hydroxyethyl ammonium methyl sulfate.

Preferred cationic surfactants are for example saturated or unsaturated fatty acid based mono-ester and di-ester quats having 10 to 18 carbon atoms in the alkyl chain. Commercially available examples are Arquad PC SV-60 PG and Armocare VGH70 (AKzo Nobel). Other examples of esterquat, are dipalmitoylethyl hydroxyethylmonium methosulfate (for example tradename stepanquat GA90) or methyl bis [ethyltallowate]-2-hydroxyethyl ammonium methyl sulfate.

Most preferred cationic surfactants are mono-long alkyl quaternized ammonium salts having the formula:

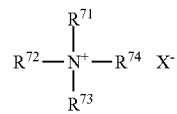

wherein one of $R^{71}$, $R^{72}$, $R^{73}$, and $R^{74}$ is selected from an aliphatic group of from about 16 to about 30 carbon atoms or an aromatic, alkoxy, polyoxyalkylene, alkylamido, hydroxyalkyl, aryl or alkylaryl group having up to about 30 carbon atoms; the remainder of $R^{71}$, $R^{72}$, $R^{73}$, and $R^{74}$ are independently selected from an aliphatic group of from about 1 to about 8 carbon atoms or an aromatic, alkoxy, polyoxyalkylene, alkylamido, hydroxyalkyl, aryl or alkylaryl group having up to about 8 carbon atoms; and X is a salt-forming anion such as those selected from halogen, (e.g., chloride, bromide), acetate, citrate, lactate, glycolate, phosphate, nitrate, sulfonate, sulfate, alkylsulfate, glutamate, and alkyl sulfonate radicals, and wherein the aliphatic groups can contain, in addition to carbon and hydrogen atoms, ether linkages, and other groups such as amino groups. The longer chain aliphatic groups, e.g., those of about 16 carbons, or higher, can be saturated or unsaturated. Preferably, one of $R^{71}$, $R^{12}$, $R^{73}$, and $R^{74}$ is selected from an alkyl group of from about 16 to about 30 carbon atoms, more preferably from about 18 to about 26 carbon atoms, still more preferably from about 22 carbon atoms; the remainder of $R^{71}$, $R^{72}$, $R^{73}$, and $R^{74}$ are independently selected from the group consisting of —$CH_3$, —$C_2H_5$, —$C_2H_4OH$, —$CH_2C_6H_5$, and mixtures thereof; and ($X^-$) is selected from the group consisting of $Cl^-$, $Br^-$, $CH_3OSO_3^-$ and mixtures thereof. Most preferred are trimethyl(C12 to C24)alkyl ammonium salts, such as cetrimonium chloride, cetrimonium bromide, behentrimonium chloride. It is believed that such mono-long alkyl quaternized ammonium salts can provide improved slippery and slick feel on wet hair, compared to multi-long alkyl quaternized ammonium salts. It is also believed that mono-long alkyl quaternized ammonium salts can provide improved hydrophobicity and smooth feel on dry hair, compared to amine or amine salt cationic surfactants.

More applicable specific cationic surfactants are disclosed e.g. in WO2009035970 (in particular at page 7, line 8 to page 17, last line) the entire disclosure of which is incorporated by reference and also in US2013/259820 (in particular paragraphs [0074] to [0078] the entire disclosure of which is incorporated by reference.

The compositions of the present invention preferably comprise the cationic surfactant B1) in amount of from about 0.01% to about 15%, preferably from about 0.05% to about 10%, still more preferably from about 0.1% to about 6%, specifically from 0.1 to 5% by weight of the composition (all percentages are by weight).

The aqueous composition according to this invention may comprise as the surfactant B) the anionic surfactant B2).

The cationic surfactants B1) and the anionic surfactants B2) are preferably not used together, but as the case may be they can be also used in mixtures thereof.

The anionic surfactant B2) is preferably selected from the group consisting of organic sulfates, organic sulfonates, organic phosphates, organic phosphonates, and organic carboxylates, such as alkyl sulfates including ammonium lauryl sulfate, sodium lauryl sulfate, alkyl-ether sulfates, including sodium laureth sulfate, and sodium myreth sulfate.

Preferred examples for anionic surfactants are organic carboxylates, organic sulfates, organic sulfonates, organic phosphates and organic phosphonates preferably containing linear or branched organic groups having C8 to C50 carbon atoms, preferred C8 to 40 carbon atoms, more preferred C8 to C24 carbon atoms, such as alkyl, fatty alcohol and fatty acid based surfactants, i.e. C8 to C24 fatty acid carboxylates, C8 to C24 fatty acid polyether carboxylates, C8 to C24 fatty acid polyether sulfates, C8 to C24 maleic acid addition products, C8 to C24 fatty alcohol sulfates, C8 to C24 sulfonates, C8 to C40 phosphates containing one or two fatty acid moieties.

Preferably, anionic surfactants suitable for use in the compositions are the alkyl and alkyl ether sulfates. Other suitable anionic surfactants are the water-soluble salts of organic sulfuric acid reaction products. Still other suitable anionic surfactants are the reaction products of fatty acids esterified with isethionic acid and neutralized with sodium hydroxide. Exemplary anionic surfactants for use in the shampoo composition include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In a further embodiment of the present invention, the anionic surfactant is sodium lauryl sulfate or sodium laureth sulfate.

Preferred anionic surfactants are saturated or unsaturated fatty alcohol based polyether sulfates having 10 to 18 carbon atoms in the alkyl chain and 2 to 30 EO units. Commercially available examples are the Emulsogen EPM types (Clariant).

Further preferred anionic surfactants are saturated or unsaturated fatty alcohol based polyether carboxylates having 10 to 18 carbon atoms in the alkyl chain and 2 to 30 EO units. Commercially available examples are the Empicol types (Huntsman).

Details on anionic surfactants are disclosed in US2015/011449 (WO2015002812A1—page 10) the entire content of which is incorporated by reference herewith, The compositions of the present invention preferably comprise the anionic surfactant B2) in amount of from about 0.05% to about 25%, preferably from about 1% to about 20%, still more preferably from about 3% to about 18%, specifically from 5 to 15% by weight of the composition (all percentages are by weight).

Further details on anionic and cationic surfactants are disclosed in US 2009-0165812 (paragraph [0040]) the entire content of which is incorporated by reference herewith.

In a preferred embodiment the aqueous compositions according to the invention comprise at least one surfactant B), which is selected from:

cationic surfactants B1), selected from quaternary ammonium compounds or amino compounds having up to 50 carbon atoms, each containing linear or branched, optionally substituted alkyl groups with up to 20 carbon atoms which optionally contain further heteroatoms, such as nitrogen, oxygen, including ester quats having at least one quaternary ammonium group and at least one ester group, such as fatty acid based ester quats containing one or two fatty acid moieties, preferably mono (C8 to C20 alkyl)-tri (C1 to C7 alkyl) quaternized ammonium salts, di (C8 to C20 alkyl)-di (C1 to C7) alkyl quaternized ammonium salts, wherein the alkyl groups are optionally substituted and may contain further heteroatoms such as oxygen or nitrogen, and include for example unsubstituted alkyl groups, alkyl groups carrying an aromatic group such as benzyl groups, alkyl groups carrying an alkoxy group, alkyl groups carrying an ether moiety, such as a polyoxyalkylene moiety, alkyl groups carrying an amino or amido group, alkyl groups carrying a hydroxy group, and the counter ion is a salt-forming anion such as those selected from halogen, (e.g., chloride, bromide), acetate, citrate, lactate, glycolate, phosphate, nitrate, sulfonate, sulfate, alkylsulfate, glutamate, and alkyl sulfonate radicals, preferably in the quaternary ammonium compounds or amino compounds the C8 to C20 alkyl group is selected from alkyl groups having about 14 to about 20 carbon atoms, and the C1-C7 alkyl groups preferably are independently selected from the group consisting of $CH_3$, $C_2H_5$, $C_2H_4OH$, $CH_2C_6H_5$, and mixtures thereof, and the counter ion is selected from the group consisting of Cl—, Br—, $CH_3OSO_3$—, and mixtures thereof, and further preferred cationic surfactants are saturated or unsaturated fatty acid based mono-ester and di-ester quaternary ammonium compounds having 10 to 18 carbon atoms in the alkyl chain, and/or (preferably or)

anionic surfactants B2), selected from carboxylates, sulfates, sulfonates, phosphates and phosphonates having up to 50 carbon atoms, each containing linear or branched, optionally substituted alkyl groups with up to 20 carbon atoms which optionally contain further heteroatoms, such as nitrogen, oxygen, preferably linear or branched C8 to C50, preferred C8 to 40, more preferred C8 to C24 alkyl, fatty alcohol and fatty acid based surfactants, such as C8 to C24 fatty acid carboxylates, C8 to C24 fatty acid polyether carboxylates. C8 to C24 fatty alcohol polyether carboxylates, C8 to C24 fatty acid polyether sulfates, C8 to C24 fatty alcohol polyether sulfates, C8 to C24 maleic acid addition products, C8 to C24 fatty alcohol sulfates, C8 to C24 sulfonates, C8 to C40 phosphates containing one or two fatty acid moieties.

Preferably the surfactant B) has a HLB value ranging from 1 to 20, preferred 7 to 20, more preferred 8 to 20.

Depending on the chemical nature of the continuous and discontinuous phase emulsifiers having a HLB value <7 (W/O emulsion type) or >7 (O/W emulsion type) are preferably selected.

In a preferred embodiment of the invention the hair treatment composition provided is a W/O formulation.

In another preferred embodiment of the invention the hair treatment composition provided is an O/W formulation.

In addition to the surfactant B1) and B2) nonionic surfactants can be used optionally. Preferably the anionic surfactants B2) can be used together with nonionic surfactants.

Preferred examples for nonionic surfactants are ethylene oxide (EO), propylene oxide (PO) and butylene oxide (BO) containing linear or branched C8 to C50, preferred C8 to 40, more preferred C8 to C24 fatty alcohol and fatty acid based emulsifiers as well as saccharide based emulsifiers, i.e. alkyl glycosides, alkoxylated fatty acid sorbitane esters and fatty acid glucamides. Another variety of preferred nonionic surfactants are the semi-polar amine oxides, phosphine oxides, and sulfoxides.

Preferred nonionic surfactants are saturated or unsaturated natural alcohol based ethoxylates having 10 to 18 carbon atoms in the alkyl chain and 5 to 80 EO units. Commercially available examples are the Genapol C, LA, V, O and T types (Clariant).

Preferred nonionic surfactants are linear or branched oxo alcohol based ethoxylates having 11 to 17 carbon atoms in the alkyl chain and 5 to 100 EO units. Commercially available examples are the Genapol UD, OA, OX, X, LCN types (Clariant).

Preferred nonionic surfactants are saturated or unsaturated alcohol based block ethoxylates-propoylates having 10 to 18 carbon atoms in the alkyl chain and 2 to 20 EO units. Commercially available examples are the Genapol EP types (Clariant).

Preferred nonionic surfactants are ethoxylate-propylate block copolymers containing 5 to 70% wt % EO units. Commercially available examples are the Genapol PF and PH types (Clariant).

Preferred nonionic surfactants are saturated or unsaturated fatty acid based ethoxylates having 10 to 18 carbon atoms in the alkyl chain and 5 to 100 EO units. Commercially available examples are the Genagen O and S types (Clariant).

Preferred nonionic surfactants are saturated or unsaturated fatty acid based castor oil ethoxylates having 10 to 18 carbon atoms in the alkyl chains and 5 to 80 EO units. Commercially available examples are the Emulsogen HCO and EL types (Clariant).

Preferred nonionic surfactants are saturated or unsaturated fatty acid derivatized oligoglycerines. Preferred examples are fatty acid derivatized di-, tri-, or tetraglycerines, i.e. mono- or diesters of diglycerine having having 10 to 18 carbon atoms in the alkyl chain and optionally 5 to 100 EO units. Commercially available examples are the Hostacerine types (Clariant).

Preferred nonionic surfactants are saturated or unsaturated fatty acid sorbitane ester based ethoxylates having 10 to 18 carbon atoms in the alkyl chain and 5 to 50 EO units attached to the sorbitane ring. A commercially available example is Emulsogen 4156 (Clariant).

Preferred nonionic surfactants are saturated or unsaturated alcohol based glycosides having 8 to 18 carbon atoms in the alkyl chain and 1 to 10 glycosyl units. Commercially available examples are Plantacare 818up and 1200up (BASF).

Preferred nonionic surfactants are saturated or unsaturated fatty acid based glucamides, preferred fatty acid N-methylglucamides, having 8 to 18 carbon atoms in the alkyl chain. A commercially available example is the MEGA-10 type (Avanti).

Preferred nonionic surfactants are saturated or unsaturated fatty acid based alkanolamides, preferred fatty acid based ethanolamides, having 8 to 18 carbon atoms in the alkyl chain. Commercially available examples are the Aminon C types (Kao).

Preferred nonionic surfactants are the fatty amine or fatty acid amide based amine oxides having 8 to 30 carbon atoms in the alkyl chain. Commercially available examples are the Tomamine AO types (Air products) and the Genamineox types (Clariant).

The compositions of the present invention preferably may comprise the nonionic surfactant in amount of from about 0% to about 15%, preferably from about 0% to about 5%, still more preferably from about 0% to about 5%, specifically from 0 to 3% by weight of the composition (all percentages are by weight). If they are used the amount is generally above 0.1% by weight.

In addition to the surfactant B1) and B2) betaine-type surfactants can be used optionally. Preferably the betaine-type surfactants can be used together with anionic surfactants B2).

Preferred examples for betaine emulsifiers are carbobetaine, sulfobetaine, phosphatobetaine and phosphonatobetaine groups containing linear or branched C8 to C50, preferred C8 to 40, more preferred C8 to C30 alkyl, fatty alcohol and fatty acid based emulsifiers, i.e. cocoamidopropyl carbobetaines.

Preferably, suitable betaine surfactants for use in compositions according to the invention include those which are known for use in shampoo or other personal care cleansing. They include those surfactants broadly described as derivatives of aliphatic secondary and tertiary amines in which the aliphatic radical can be straight or branched chain and wherein one of the aliphatic substituents contains from about 8 to about 30 carbon atoms and one contains an anionic group such as carboxy, sulfonate, sulfate, phosphate, or phosphonate. Exemplary amphoteric surfactants for use in the formulations of the present invention include cocoamphoacetate, cocoamphodiacetate, lauroamphoacetate, lauroamphodiacetate, and mixtures thereof.

They also include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 30 carbon atoms and one contains an anionic group such as carboxy, sulfonate, sulfate, phosphate or phosphonate.

Preferred carbobetaine surfactants are saturated or unsaturated fatty acid based sarcosides having 10 to 18 carbon atoms in the alkyl chain. A commercially available example is Medialan LD (Clariant).

Preferred carbobetaine surfactants are saturated or unsaturated fatty acid based amido propyl betaines having 10 to 18 carbon atoms in the alkyl chain. A commercially available example is Genagen CAB (Clariant).

Preferred sulfobetaine surfactants are saturated or unsaturated fatty acid based taurides having 10 to 18 carbon atoms in the alkyl chain. A commercially available example is Hostapon CT (Clariant).

Details on betaine surfactants are disclosed in US2015/011449.

The compositions of the present invention preferably comprise the betaine surfactant in amount of from about 0% to about 15%, preferably from about 0% to about 5%, still more preferably from about 0% to about 5%, specifically from 0 to 3% by weight of the composition (all percentages are by weight). If they are used the amount is generally 0.1% by weight or more.

Also silicone based surfactants can be used which can be cationic, nonionoic, betaine and anionic surfactants. If they are cationic they belong to component B1), if they are anionic they belong to component B2). However, components B1) and B2) preferably do not comprise silicone based surfactants. It is possible to use the cationic or anionic silicone based surfactants in admixture with components B1) and B2) which are non-silicone-based surfactants.

Preferred examples for cationic silicone based emulsifiers are quaternary ammonium groups or amino groups containing emulsifiers of the ABA type with EO/PO moieties attached to the terminal quat or amino ends of a silicone chain (WO2009/042083) or quat/amino emulsifiers having polyether moieties attached to the silicone chain in a comb like arrangement (US2008/213208).

In another preferred embodiment of the invention hydrophilic polyhydroxy moieties as well as oleophilic fatty alkyl or fatty alkyl ester moieties are attached to the silicone chain (US2012/289649). A commercially available example for this type of W/O emulsifier is Silform EOF (Momentive Performance Materials).

Preferred examples for siloxane based nonionic emulsifiers are ethylene oxide (EO), propylene oxide (PO) and butylene oxide (BO) containing emulsifiers of the ABA type with EO/PO/BO moieties attached to the terminal ends of a silicone chain or emulsifiers having polyether moieties attached to the silicone chain in a comb like arrangement. A commercially available example is SF 1540 (Momentive Performance Materials), In another preferred embodiment of the invention hydrophilic polyether moieties as well as oleophilic alkyl chains are attached to the silicone chain (U.S. Pat. No. 4,698,178). In another preferred embodiment of the invention hydrophilic polyglycerol moieties as well as alkyl or fatty alcohol ether/fatty acid ester moieties are attached to the silicone chain (US2010/0266651, US2009/0062459). In another preferred embodiment of the invention amodimethicone glycerocarbamates are used (SÖFW-Journal, 132, 12-2006, 31). In another preferred embodiment of the invention cetyl diglyceryl tris(trimethylsiloxy)silylethyl dimethicones are used (http://ec.euroa.eu/consumers/cosmetics/cosing/index.cfm?fuseaction=searh.details_v2id=9 2003).

The latter four types of emulsifier are especially preferred for W/O emulsions.

The amounts of such silicone based surfactants correspond to what is indicated for the cationic, nonionoic, betaine and anionic surfactants above. It is within the scope of the invention to use more than one surfactant in order to optimize the formulation stability.

The aqueous compositions according to the invention optionally comprise at least one or more additional additive, selected from:

C) organic diluents or solvents (also referred to as non-aqueous diluent C)),
D) proteins, preferably keratin,
E) emollients or fatty substances,
F) preservatives,
G) skin protecting ingredients,
H) conditioning agents,
I) oxidizing agents,
J) reducing agents,
K) tannins,
L) metal salts,
M) further auxiliaries selected from pH adjusting agents, thickeners, lipids, amino acids, sugars, fragrances, sunscreen agents, vitamins, pearlescent agents, gelling agents, trace elements, sequestering agents, antioxidants, humectants, anti-hair loss agents, antidandruff agents, propellants, ceramides, polymers, in particular film-forming polymers, fillers, nacres, colorants, in particular pigments and dyes, and mixtures thereof,
   with the proviso that oxidizing agents and reducing agents are not present simultaneously in a given formulation.

C) Organic Diluents or Solvents

The term "organic diluents or solvents" refers to substances that may be used in particular to dilute/solvatize the at least one polyorganosiloxane A) according to the invention and the other optional other ingredients as mentioned before in addition to water in the aqueous compositions. Suitable organic solvents are e.g. 2-methyl-1,3-propanediol, mono and dialcohols or the ethers and esters thereof, in particular mono-C1-C3-alkyl ether, ethanol, n-propanol, isopropyl alcohol, tert, butanol, 1-methoxypropanol, 1-ethoxypropanol and ethoxydiglycol, diols and their ethers and esters, propylene glycol (1,2-propanediol), 1,3- and 1,4-butanediol, pentylene glycol, hexylene glycol, diethyleneglycol and the monomethyl and monoethyl ether thereof, such as propylene glycol mono methyl ether, dipropylene glycol and the monomethyl and monoethyl ether thereof, glycerol, diglycerol, hexanetriol, sorbitol, ethyl carbitol, benzyl alcohol, benzyloxy ethanol, propylene carbonate, N-alkyl pyrrolidone. In a preferred embodiment water/ethanol, water/isopropyl alcohol, water/dipropylene glycol, water/propylene glycol mono methyl ether and water/dipropylene glycol/propylene glycol mono methyl ether mixtures are used in the aqueous compositions of the invention. Generally, the addition of certain amounts of short chained alcohols improves the homogeneity of the formulations and the penetration of the formulations into the hair.

D) Protein/Keratin

The optional protein, preferred keratin protein fractions used comprise hydrolyzed keratin produced by alkaline and/or enzymatic hydrolysis using methods known in the art. The keratin hydrolysate is about 1,000-3,000 molecular weight. The keratin may be derived from human or other mammalian sources such as goat hair (US 2007-0048235), hoof or horn meals, (U.S. Pat. No. 6,555,505). Alternatively, "keratin protein fraction" is a purified form of keratin that contains predominantly, although not entirely, one distinct protein group as described in U.S. Pat. No. 7,148,327. Details on the keratin and keratin fractions are disclosed in US 2009-0165812.

E) Emollients, Fatty Substances

A further optional ingredient of the hair treatment formulations is one or more emollients. An "emollient" is a material that protects the skin against wetness or irritation, softens, smoothes, supples, coats, lubricates, moisturizes, protects and/or cleanses the skin. Emollients include for example: a silicone compound, i.e dimethicones, cyclomethicones, preferred $D_5$ and $D_6$ cyclosiloxanes, dimethicone copolyols or mixtures of cyclomethicones and dimethicone/vinyldimethicone cross polymer), polyols such as sorbitol, glycerin, propylene glycol, ethylene glycol, polyethylene glycol, caprylyl glycol, polypropylene glycol, 1,3-butane diol, hexylene glycol, isoprene glycol, xylitol, ethylhexyl palmitate, a triglyceride such as caprylic/capric triglyceride and fatty acid ester such as cetearyl isononanoate or cetyl palmitate. Details on emollients are disclosed in US 2009/0165812.

As fatty substances that are liquid at ambient temperature, often referred to as oils, that can be used in the invention, mention may be made of: hydrocarbon-based oils of animal origin, such as perhydrosqualene, hydrocarbon-based plant oils, such as liquid triglycerides of fatty acids containing 4 to 10 carbon atoms, for instance heptanoic or octanoic acid triglycerides, or else sunflower oil, maize oil, soya oil, grapeseed oil, sesame oil, apricot oil, macadamia oil, castor oil, avocado oil, caprylic/capric acid triglycerides, jojoba oil, shea butter; linear or branched hydrocarbons of mineral or synthetic origin, such as liquid paraffins and derivatives thereof, petroleum jelly, polydecenes, hydrogenated polyisobutene such as Parlearrm; synthetic esters and ethers, in particular of fatty acids, for instance purcellin oil, isopropyl myristate, 2-ethylhexyl palmitate, 2-octyldodecyl stearate, 2-octyldodecyl erucate, isostearyl isostearate, hydroxylated esters, for instance isostearyl lactate, octyl hydroxystearate, octyldodecyl hydroxystearate, diisostearyl malate, triisocetyl citrate, fatty alcohol heptanoate, octanoate and decanoate; polyol ester, for instance propylene glycol dioctanoate, neopentyl glycol diheptanoate, diethylene glycol diisononanoate, pentaerythritol esters, fatty alcohols having 12 to 26 carbon atoms, for instance octyldodecanol, 2-butyloctanol, 2-hexyldecanol, 2-undecyl pentadecanol, oleyl alcohol, partially hydrocarbon-based and/or silicone-based fluoro oils, silicone oils, for instance volatile or non-volatile, linear or cyclic polydimethylsiloxanes (PDMS) which are liquid or pasty at ambient temperature (25° C.), such as cyclomethicones, dimethicones, optionally comprising a phenyl group, for instance phenyl trimethicones, phenyl trimethylsiloxydiphenylsiloxanes, diphenylmethyl-dimethyltrisiloxanes, diphenyl dimethicones, phenyl dimethicones, polymethylphenylsiloxanes; mixtures thereof. Details on suitable fatty substances are disclosed in WO 2012-038334.

F) Preservatives

Optionally, one or more preservatives may be included in the hair treatment formulations. Examples of such preservatives comprise one or more glycerin containing compound (e.g., glycerin or ethylhexylglycerin or phenoxyethanol), lactic acid, benzyl alcohol, EDTA, potassium sorbate and/or grapefruit seed extract. In a preferred embodiment, the hair straightening formulations are paraben free. Details on preservatives are disclosed in US 2009/0165812.

G) Skin Protecting Agents

Optionally, the hair treatment formulations comprise one or more skin protecting agents. Skin protecting agents comprise one or more agents that prevent the undesired transmission of microbes or organic/inorganic chemicals. Details on skin protecting agents are disclosed in US 2009/0165812.

H) Conditioning Agents

Optionally, one or more conditioning agent may be included in the hair treatment formulations. In one preferred embodiment silicone based conditioning agents are incorporated. Preferred materials are PDMS grades ranging from 10 to 1,000,000 mPa·s, C2 to C18-alkyl derivatized silicones, dimethiconols, polyether modified silicones, amino groups or quaternized ammonium groups containing silicones. They may be also selected from polyorganosiloxanes having functional groups FA as defined above. These silicones can be incorporated as neat materials, organic solutions, emulsions or microemulsions.

Preferred examples for quaternary ammonium groups (quats) containing conditioning agents are α,ω-quat group terminated silicones (U.S. Pat. No. 4,891,166), quat group terminated T shaped silicones (US2008027202), α,ω-silicone block terminated quats (WO02/10256) and silicones containing quat groups in a comb like arrangement, optionally containing additional moieties, i.e. polyethers or aromatic structures (US2008213208, U.S. Pat. Nos. 5,098,979, 5,153,294, 5,166,297, US2006188456). Other preferred examples are quat group/silicone block based copolymers (EP282720, U.S. Pat. Nos. 6,240,929, 6,730,766, DE102004002208). In another preferred embodiment quat group/silicone block/hydrophilic block based copolymers are used (WO 02/10257 and WO 02/10259, U.S. Pat. Nos. 7,563,856, 7,563,857, US20110039948, US2007106045, US2005255073, WO2004069137). Other preferred examples are quat group/silicone block based copolymers and quat group/silicone block/hydrophilic block based copolymers bearing terminal monofunctional silicone moieties (WO2013148629, WO2013148635, WO2013148935). In another preferred embodiment of the invention quat group terminated silicones bearing pending amino groups are used (DE10253152). Other preferred examples are silicone betaines (DE10036522, DE10036532). Commercially available examples for quaternary ammonium groups containing siloxanes are Silsoft Silk, Silsoft Q (Momentive Performance Materials).

The above described silicone based conditioning agents in particular impart a smooth and silky feel to hair.

Alternatively, hydrocarbon based conditioning agents can be included. Details on these cationic types of material, containing amino and/or quaternary ammonium groups are disclosed for example in US 2009/0000638 and WO 2012/027369.

I) Oxidizing Agents

Optionally, one or more oxidizing agent may be included in the hair treatment formulations. Preferred oxidizing agents include organic oxidizers. i.e. benzoquinone, other quinone derivatives including hydroquinone and aminoquinones and suitable organic peroxides. Details on organic oxidizers are disclosed in US 2012/0031420 and WO 2012/027369.

Hydrogen peroxide is the preferred inorganic oxidizing agent. Persulfates, in the form of their sodium potassium and ammonium salts, may also be used alone or in combination with the hydrogen peroxide just before use. Other possible oxidizing agents include sodium percarbonate, sodium perborate, magnesium perborate, magnesium dioxide and barium dioxide. Details on these oxidizing agents are disclosed in U.S. Pat. No. 6,544,499.

J) Reducing Agents

Optionally, one or more reducing agent may be included in the hair treatment formulations with the proviso that oxidizing agents and reducing agents are not present simulatenously in a given formulation. Preferred reducing agents are thioglycolic acid and thiolactic acid as well as the salts thereof, in particular the ammonium and ethanolamine salts. Further useful thio compounds are in particular cysteine or the hydrochloride thereof, homocysteine, cysteamine, N-acetyl cysteine, thioglycerol, ethanediol monothioglycollate, 1,2-propyleneglycol monothioglycollate (see also WO 93/1791), 1-3-propanediol monothioglycollate or the isomer mixture resulting therefrom, 1,3-butanediol and 1,4-butanediol monothioglycollate and the isomer mixtures therefrom, polyethylene glycol, such as di-, tri- and tetraethyleneglycol monothioglycollates, glycerol monothiolactate and further thio acids and the esters thereof, as well as mixtures thereof. Details on these organic reducing agents are disclosed in US 2009/0000638.

The usage of inorganic reducing sulfur compounds is basically also possible.

Representative examples for use in the reducing compositions include cosmetically acceptable salts (e.g., alkali metal (e.g., sodium and potassium) and ammonium salts), esters (e.g., lower alkyl amines (e.g., triethanolamine (TEA), monoethanolamine (MEA) and aminomethyl propanol (AMP), of sulfite, disulfite, bisulfite, metabisulfite, hydrosulfite, hyposulfite and pyrosulfite). Specific examples of suitable reducing agents thus include sodium metabisulfite, potassium metabisulfite, sodium sulfite, potassium sulfite, sodium thiosulfate, potassium thiosulfate, ammonium bisulfate, ammonium sulfite, ammonium metabisulfite, MEA sulfite, MEA metabisulfite, potassium bisulfite, sodium bisulfite, ammonium bisulfite, sodium hydrosulfite, potassium hydrosulfite, ammonium hydrosulfite, anhydrous sodium sulfite, diammonium sulfite, dipotassium disulfite, dipotassium pyrosulfite, AMP sulfite, AMP metabisulfite, TEA sulfite, TEA metabisulfite, sodium acid sulfite, sodium hyposulfite, sodium pyrosulfite, and sodium thiosulfate pentahydrate. Details on these inorganic reducing agents are disclosed in WO 2012/027369.

Alternatively, high temperature and alkali-treated keratin, wherein the keratin is heated to around 100° C. or above, dithionites and certain hydrides can be used. Details on these reducing agents are disclosed in U.S. Pat. No. 6,544,499.

K) Tannins

Optionally one or more tannins, specifically gallotannins, ellagitannins, complex tannins, condensed tannins, i.e. tannic acid and its other forms quercitannic acid and gallotannic acid may be used. Tannins represent a class of polyphenol derivatives and are known for their structural diversity. A classification is given based on K. Khanbabaee, T. van Ree, Nat. Prod. Rep., 2001, 18, 641-649 which is herewith included by reference. The most preferred tannin is gallotannic acid (=tannic acid). Preferred tannins include:

Gallotannins (1), Ellagitannins (2), Complex Tannins (3), and Condensed Tannins (4)

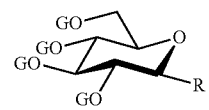

R = α,β-OH, 55
R = β-OG, 56

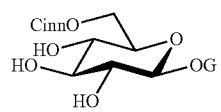

57

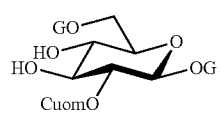

58

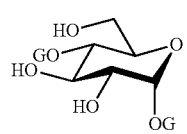

59

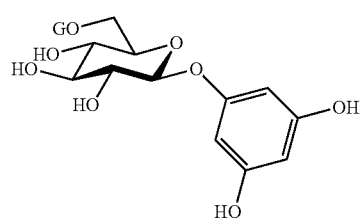

60

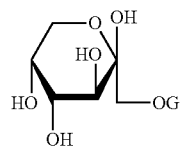

61

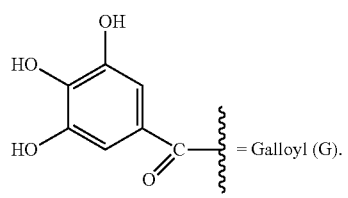

62

= Galloyl (G).

Examples for ellagitannins are
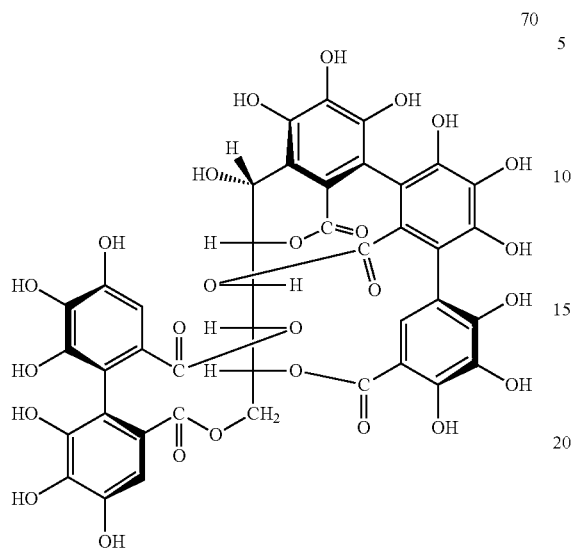
70
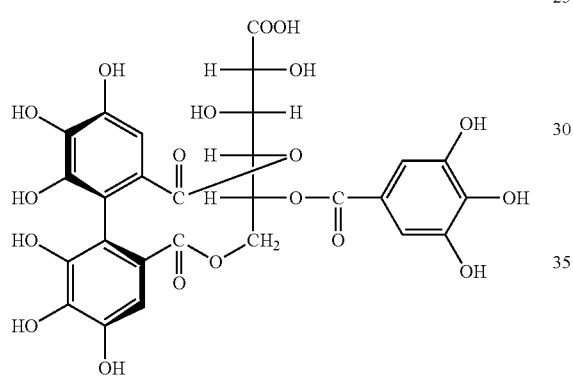
71
An example for a complex tannin is Acutissimin A
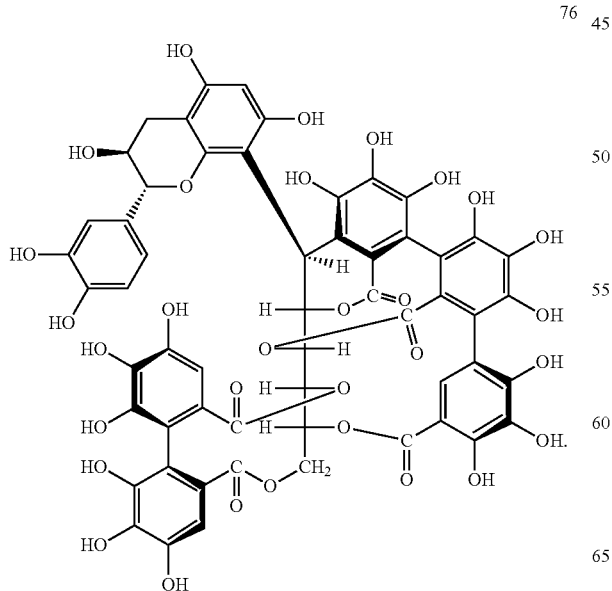
76
Examples for condensed tannins are procyanidin B2 (77), proanthocyanidin A1 (78), proanthocyanidin A2 (79) and proanthocyanidin C1 (80):
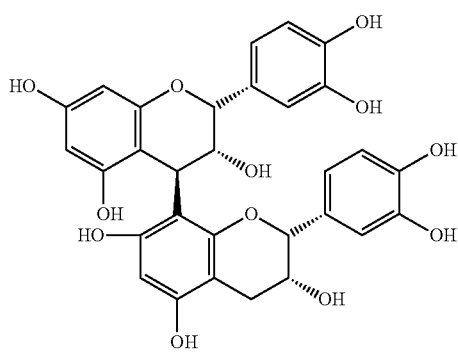
77
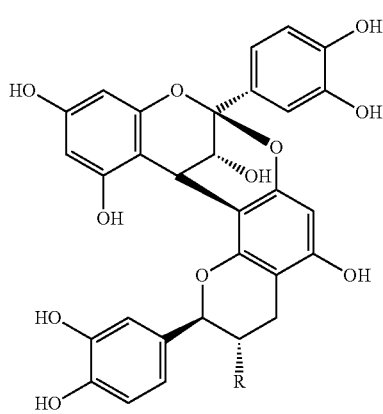
R = ·····ıııOH; 78
R = ━━OH; 79
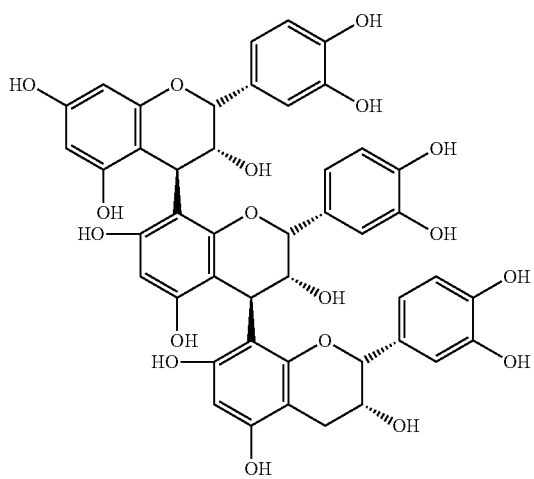
80

The most preferred tannin is tannic acid:

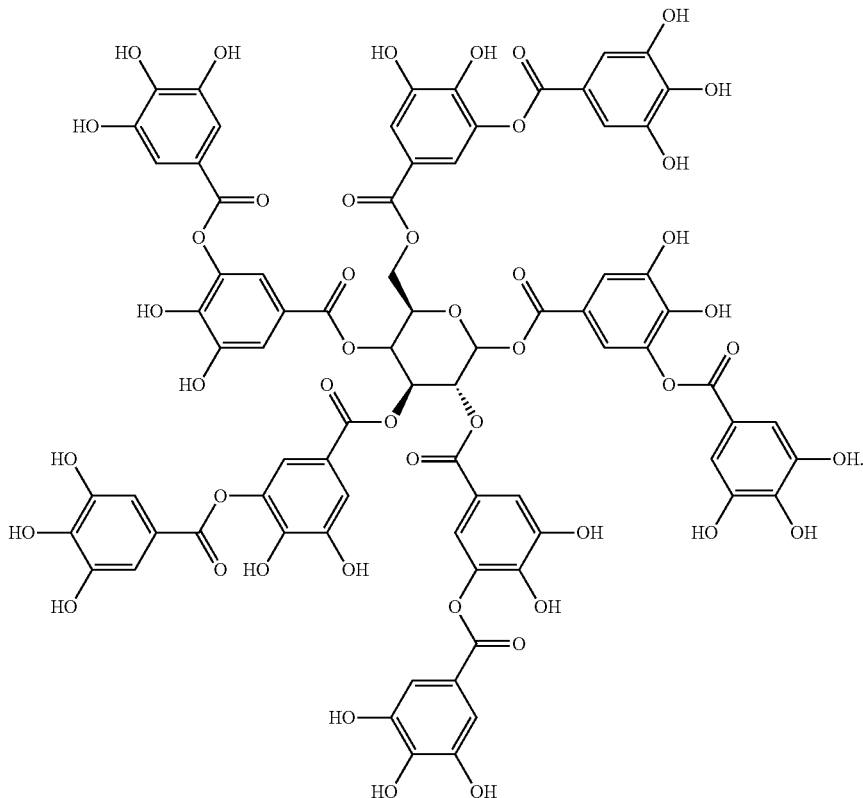 [SMILES: O=C(OC[C@H]1OC(OC(=O)c2cc(O)c(O)c(OC(=O)c3cc(O)c(O)c(O)c3)c2)[C@H](OC(=O)c2cc(O)c(O)c(OC(=O)c3cc(O)c(O)c(O)c3)c2)[C@@H](OC(=O)c2cc(O)c(O)c(OC(=O)c3cc(O)c(O)c(O)c3)c2)C1OC(=O)c1cc(O)c(O)c(OC(=O)c2cc(O)c(O)c(O)c2)c1)c1cc(O)c(O)c(OC(=O)c2cc(O)c(O)c(O)c2)c1]

L) Metal Salts

Metal salts include in particular those of general formula:

Me(A⁻)$_n$ wherein Me is the cation of a metal of valence n, n is 2 or 3, preferably Zn or Fe, each A⁻ independently is (i) the anion of an oxidized carbohydrate of the formula ⁻O—C(O)—R⁴ in which R⁴ is the residue of the same or different carbohydrate, or (ii) an anion derived from an inorganic or organic acid. Particular preferred salts are $Fe^{2+}$ lactobionate, $Fe^{2+}$ maltobionate, $Fe^{2+}$ isomaltobionate, $Fe^{3+}$ lactobionate, $Fe^{3+}$ maltobionate, $Fe^{3+}$ isomaltobionate, $Fe^{2+}$ gluconate, $Fe^{3+}$ gluconate, $Fe^{2+}$ glucoheptonate, $Fe^{3+}$ glucoheptonate, $Fe^{2+}$ glycerophosphate, $Fe^{3+}$ glycerophosphate, $Zn^{2+}$ lactobionate, $Zn^{2+}$ maltobionate, $Zn^{3+}$ isomaltobionate, $Zn^{2+}$ gluconate, and $Zn^{2+}$ glycerophosphate.

These metal salts act in particular as hair strengthening additive.

Preferred are metal salts of Fe and/or Zn, in particular water-soluble metal salts of Fe and/or Zn, preferably $Zn^{2+}$, $Fe^{2+}$ or $Fe^{3+}$ salts with counter ions preferably selected from:
chloride, sulphate, alkylsulphonate, arysulphonate, alkylarylsulphonate, anions derived from hydroxy functionalized carboxylic acids, specifically derived from
C2 to C12, preferred C2 to C9 saturated or unsaturated hydroxyalkyl carboxylic acids, i.e. glycolic acid, lactic acid, γ-hydroxy butyric acid, γ-hydroxy butyric acid, 2-hydroxysuccinic acid, citric acid, mandelic acid,
C2 to C12, preferred C2 to C9, also preferred C7 to C12, more preferred C7 to C9 saturated or unsaturated polyhydroxyalkyl carboxylic acids, i.e. glyceric acid, 2,2-dimethylolpropane carboxylic acid, arabinonic acid, gluconic acid, glucoronic acid, glucoheptonic acid, glucopyranosyl arabinonic acid, lactobionic acid, maltobionic acid, tartaric acid,
C7 to C12, preferred C7 to C9 hydroxyaromatic carboxylic acids, i.e. 2-hydroxy benzoic acid, 3-hydroxy benzoic acid, 4-hydroxy benzoic acid, 2-hydroxy cinnamic acid, 3-hydroxy cinnamic acid, 4-hydroxy cinnamic acid,
C7 to C12, preferred C7 to C9 polyhydroxyaromatic carboxylic acids, i.e 2,3-dihydroxy benzoic acid, 2,4-dihydroxy benzoic acid, 2,5-dihydroxy benzoic acid, 2,6-dihydroxy benzoic acid, 3,4-dihydroxy benzoic acid, 3,5-dihydroxy benzoic acid, dihydroxy cinnamic acids or their partial esters, i.e. 3,4-dihydroxy cinnamic acid, trihydroxy benzoic acids or their partial esters, i.e. 2,3,4-trihydroxy benzoic acid, 2,3,5-trihydroxy benzoic acid, 2,3,6-trihydroxy benzoic acid, 2,4,5-trihydroxy benzoic acid, 2,4,6-trihydroxy benzoic acid, 3,4,5-trihydroxy benzoic acid, trihydroxy cinnamic acids or their partial esters, i.e. 3,4,5-dihydroxy cinnamic acid, and mixtures thereof.

Aqueous compositions according to the invention which comprise such water soluble Fe and/or Zn salts preferably have a weight ratio of the water soluble Fe and/or Zn salt L) to the polyorganosiloxane A) of at least 0.01, preferred 0.01 to 3, more preferred 0.02 to 3, even more preferred 0.05 to 3, specifically 0.1 to 3, even more specific 0.1 to 1. In a preferred embodiment of the invention the hair treatment formulations optionally comprise metal salts L) such iron or zinc salts in a concentration range from 0 to 15%, preferred 0 to 10%, more preferred 0 to 5%, even more preferred 0 to 2%, wherein each percentage is per weight based on the total weight of the aqueous composition.

M) Further Auxiliaries

The hair treatment formulations may also comprise one or more additional auxiliaries, i.e. pH adjusting agents as described below, such acids, bases and buffers to adjust the pH value, thickeners (such as polysaccharide thickeners, starch, modified starches, xanthan, gellan, carragenan, pullulan, cellulose, cellulose derivatives, polyacrylic acids, polyacrylates copolymers, polyacrylamides, pectins, clays, fumed silica), lipids, amino acids, sugars, fragrances and/or sunscreen agents, vitamins, pearlescent agents, gelling agents, trace elements, sequestering agents, antioxidants, e.g. sulphite salts such as sodium sulphite, sodium hydrogen sulphite, sodium disulphite, sodium metabisulphite, potassium disulphite, potassium metabisulphite, potassium hydrogen sulphite; potassium bisulfite, calcium sulphite, calcium bisulphite, calcium metabisulphite, calcium hydrogen sulphite, ammonium sulfite, ammonium hydrogen sulphite, ammonium disulphite and ammonium metabisulphite which are also well accepted in the food industry (the quantity of sulfite salt is calculated from the amount of $SO_2$ which can be liberated by decomposition of the salt. The $SO_2$ amount ranges from 0 to 350 mg $SO_2$ per liter of solution, preferably from 1 to 350 mg $SO_2$ per liter of solution, more preferably from 10 to 350 mg $SO_2$ per Liter of solution and even more preferably from 10 to 200 mg $SO_2$ per liter of solution), humectants, anti-hair loss agents, anti-dandruff agents, propellants, ceramides, polymers, in particular film-forming polymers; fillers, nacres, colorants and in particular pigments and dyes, including hair dyeing agents, all kinds of bioactive phytochemicals, and also mixtures thereof.

Hair Dyeing Agents

Hair dyeing agents include commonly used oxidative or non-oxidative, temporary, semipermanent, demipermanent and permanent hair dyes. Temporary non-oxidative dyes include e.g. Acid Yellow, Acid Orange 7, Acid Yellow 1. Acid Red 33, Acid Red 92, Acid Violet 43, Acid Blue 9, Acid Black 1, which are commonly used in mixtures. Semi-Permanent Non-Oxidative Hair Dyeing Agents contain basic or cationic dyes with low molar mass, and include in particular HC Yellow No. 2, HC Red No. 3, 4-hydroxypropylamino-3-nitrophenol, N,N'-bis-(2-hydroxyethyl)-2-nitrophenylenediamine, HC Blue No. 2, Basic Red 51, Basic Red 76, Basic Brown 16, Basic Brown 17, Basic Blue 99, Basic Yellow 57. Other semipermanent dyes, include metallic and vegetables derivatives (such as Henna). The metallic dyes are derived from silver salts, lead, and bismuth. Permanent Oxidative Hair Dyeing Agents include commonly used complex systems of precursors in the presence of an oxidizing agent.

Depending on the polymer structure type and the application purpose certain quantities on acids, bases and/or short chained alcohols are required in order to get transparent formulations. Suitable acids include inorganic or organic acids, like for example carboxyl acids, like acetic acid, hydrochloric acid, sulfuric acid, and phosphoric acid. Suitable bases include aqueous ammonia, alkaline hydroxides, alkaline carbonates, etc.

Preferred aqueous compositions according to the invention, comprise the components A)-M) in the following amounts:

| | Ingredient | Weight-% |
|---|---|---|
| A) | polyorganosiloxane | 0.01 to 40, preferably 0.05 to 30 |
| B) | Surfactants B1) + B2) | 0.01 to 30, more preferably 0.01 to 20, even more preferably 0.05 to 15 |
| C) | diluents/solvents | 0 to 95, preferably 0.1 to 95 |
| D) | protein, preferred keratin | 0 to 15, preferably 0.1 to 15 |
| E) | emollients/fatty substance | 0 to 15 preferably 0.1 to 15 |
| F) | preservatives | 0 to 5 preferably 0.1 to 15 |
| G) | skin protecting ingredients | 0 to 15 preferably 0.1 to 15 |
| H) | conditioning agents | 0 to 15 preferably 0.1 to 15 |
| I) | oxidizing agents | 0 to 15 preferably 0.1 to 15 |
| J) | reducing agents | 0 to 15 preferably 0.1 to 15 |
| K) | tannins | 0 to 15 preferably 0.1 to 15 |
| L) | Metals salts, preferably water soluble Fe and/or Zn salts | 0 to 15 preferably 0.1 to 15 |
| M) | further auxiliaries | 0 to 25, preferably 0.1 to 15 |

In a preferred embodiment of the invention, the hair treatment formulations (which term is used as a synonym for the aqueous composition for hair treatment according to the present invention in this text) comprises the polyorganosiloxane A) in a concentration range from 0.05 to 30%, preferred 0.5 to 30%, more preferred 1 to 30%, even more preferred 1 to 20%, specifically 1 to 10%, wherein each percentage is per weight based on the total weight of the aqueous composition.

In a preferred embodiment of the invention the hair treatment formulations comprise the surfactants B1) in a concentration range from 0.01 to 15%, preferred 0.05 to 15%, more preferred 0.1 to 5%, even more preferred 0.1 to 3%, wherein each percentage is per weight based on the total weight of the aqueous composition.

In a preferred embodiment of the invention the hair treatment formulations comprise the surfactants B2) in a concentration range from 0.01 to 20%, preferred 0.05 to 15%, wherein each percentage is per weight based on the total weight of the aqueous composition.

In a preferred embodiment of the invention the hair treatment formulations optionally comprise the organic diluents/solvents C) in a concentration range from 0 to 98%, preferably 0.1 to 95%, preferred 10 to 95%, more preferred 20 to 95%, even more preferred 20 to 50% and 50 to 95%, wherein each percentage is per weight based on the total weight of the aqueous composition. In a preferred embodiment the hair treatment formulations do not comprise ethanol.

In a preferred embodiment of the invention the hair treatment formulations optionally comprise the protein D), preferred keratin in a concentration range from 0 to 15%, preferred 0 to 10%, more preferred 0 to 5%, wherein each percentage is per weight based on the total weight of the aqueous composition.

In a preferred embodiment of the invention the hair treatment formulations optionally comprise the emollients/fatty substance E) in a concentration range from 0 to 15%, preferred 0 to 10%, more preferred 0 to 5%, wherein each percentage is per weight based on the total weight of the aqueous composition.

In a preferred embodiment of the invention the hair treatment formulations optionally comprise the preservatives F) in a concentration range from 0 to 5%, preferred 0 to 3%, more preferred 0 to 2%, even more preferred 0 to 1%, wherein each percentage is per weight based on the total weight of the aqueous composition.

In a preferred embodiment of the invention the hair treatment formulations optionally comprise the skin protecting ingredients G) in a concentration range from 0 to 15%, preferred 0 to 10%, more preferred 0 to 5%, even more preferred 0 to 1%, specifically 0 to 0.1%, wherein each percentage is per weight based on the total weight of the aqueous composition.

In a preferred embodiment of the invention the hair treatment formulations optionally comprise the conditioning agents H) in a concentration range from 0 to 15%, preferred 0 to 10%, more preferred 0 to 5%, even more preferred 0 to 1%, specifically 0 to 0.1%, wherein each percentage is per weight based on the total weight of the aqueous composition.

In a preferred embodiment of the invention the hair treatment formulations optionally comprise the oxidizing agents I) in a concentration range from 0 to 15%, preferred 0 to 10%, more preferred 0 to 5%, even more preferred 0 to 2%, wherein each percentage is per weight based on the total weight of the aqueous composition.

In a preferred embodiment of the invention the hair treatment formulations optionally comprise the reducing agents J) in a concentration range from 0 to 15%, preferred 0 to 10%, more preferred 0 to 5%, even more preferred 0 to 2%, wherein each percentage is per weight based on the total weight of the aqueous composition.

In a preferred embodiment of the invention the hair treatment formulations optionally comprise tannins K) in a concentration range from 0 to 15%, preferred 0 to 10%, more preferred 0 to 5%, even more preferred 0 to 2%, wherein each percentage is per weight based on the total weight of the aqueous composition.

In a preferred embodiment of the invention the hair treatment formulations optionally comprise metal salts L) such iron or zinc salts in a concentration range from 0 to 15%, preferred 0 to 10%, more preferred 0 to 5%, even more preferred 0 to 2%, wherein each percentage is per weight based on the total weight of the aqueous composition.

In a preferred embodiment of the invention the hair treatment formulations optionally comprise the other auxiliary agents M), which are commonly known for hair care compositions and are different from the aforementioned additives, in a concentration range from 0 to 25%, preferred 0 to 10%, more preferred 0 to 5%, even more preferred 0 to 2%, wherein each percentage is per weight based on the total weight of the aqueous composition. If an auxiliary agents M) is used the amount is preferably at least 0.1% based on the total weight of the aqueous composition.

In a preferred embodiment of the invention the hair treatment formulations optionally comprise hair dyeing agents in a concentration range from 0 to 15%, preferred 0 to 10%, more preferred 0 to 5%, even more preferred 0 to 2%, wherein each percentage is per weight based on the total weight of the aqueous composition.

The above described aqueous hair treatment formulations according to the invention can provide particularly benefits with respect to an improved durability of artificial colors on hair. In addition the aqueous hair treatment formulations according to the invention provide a hair strengthening and shaping effect as well as a conditioning effect, in particular, before, during and after a hair dyeing treatment, such as hair bleaching treatment.

The present invention further relates to hair treatment compositions, comprising the aqueous compositions according to the invention. Hair treatment compositions according to the invention are selected for example from a hair shampoo, a hair care composition, a hair conditioning composition, a hair strengthening composition, a hair coloration composition, a hair color protection composition, a hair repair balm, a hair protection composition, and a hair anti-pollution treatment composition.

The present invention further relates to a hair treatment process comprising the step of contacting the hair with at least one aqueous composition or hair treatment composition as defined above.

A particularly preferred hair treatment process comprises the step of contacting the hair with at least one aqueous composition or hair treatment composition containing at least one $Zn^{2+}$, $Fe^{2+}$ and/or $Fe^{3+}$ salt, and with counter ions preferably selected from chloride, sulphate, alkylsulphonate, arylsulphonate, alkylarylsulphonate, hydroxy functionalized carboxylic acid anions, specifically derived from C2 to C12, preferred C2 to C9 saturated or unsaturated hydroxyalkyl carboxylic acids, i.e. glycolic acid, lactic acid, γ-hydroxy butyric acid, γ-hydroxy butyric acid, 2-hydroxysuccinic acid, citric acid, mandelic acid, C2 to C12, preferred C2 to C9, also preferred C7 to C12, more preferred C7 to C9 saturated or unsaturated polyhydroxyalkyl carboxylic acids, i.e. glyceric acid, 2,2-dimethylolpropane carboxylic acid, arabinonic acid, gluconic acid, glucoronic acid, glucoheptonic acid, glucopyranosyl arabinonic acid, lactobionic acid, maltobionic acid, tartaric acid, C7 to C12, preferred C7 to C9 hydroxyaromatic carboxylic acids, i.e. 2-hydroxy benzoic acid, 3-hydroxy benzoic acid, 4-hydroxy benzoic acid, 2-hydroxy cinnamic acid, 3-hydroxy cinnamic acid, 4-hydroxy cinnamic acid, C7 to C12, preferred C7 to C9 polyhydroxyaromatic carboxylic acids, i.e 2,3-dihydroxy benzoic acid, 2,4-dihydroxy benzoic acid, 2,5-dihydroxy benzoic acid, 2,6-dihydroxy benzoic acid, 3,4-dihydroxy benzoic acid, 3,5-dihydroxy benzoic acid, dihydroxy cinnamic acids or their partial esters, i.e. 3,4-dihydroxy cinnamic acid, trihydroxy benzoic acids or their partial esters, i.e. 2,3,4-trihydroxy benzoic acid, 2,3,5-trihydroxy benzoic acid, 2,3,6-trihydroxy benzoic acid, 2,4,5-trihydroxy benzoic acid, 2,4,6-trihydroxy benzoic acid, 3,4,5-trihydroxy benzoic acid, trihydroxy cinnamic acids or their partial esters, i.e. 3,4,5-dihydroxy cinnamic acid, and mixtures thereof.

Such hair treatment process preferably comprises in addition the step of drying the hair at >1500° C., i.e. during a hot ironing step, which permanently bonds to the hair or incorporates into the hair the aqueous compositions or hair treatment compositions as defined above.

In the hair treatment process described before, the weight ratio of the Fe and/or Zn salts to the polyorganosiloxane A) is preferably at least 0.01, preferred 0.01 to 3, more preferred 0.02 to 3, even more preferred 0.05 to 3, specifically 0.1 to 3, even more specific 0.1 to 1, and if the optional tannins are used, then the weight ratio of the Fe or Zn salt to the polyorganosiloxane A)+tannins is at least 0.01, preferred 0.01 to 3, more preferred 0.02 to 3, even more preferred 0.05 to 3, specifically 0.1 to 3, even more specific 0.1 to 1.

In the hair treatment process according to the invention the step of contacting the hair with the aqueous compositions or hair treatment composition, as defined above, to form the treated hair is preferably carried out at a temperature and length of time sufficient to penetrate the hair, typically at 10 to 50° C., preferred at 20 to 50° C., even more preferred room temperature (25° C.), for 5 to 120 min, preferred 5 to 60 min, even more preferred 10 to 40 min, the step of contacting the hair with the aqueous composition containing at least one $Zn^{2+}$, $Fe^{2+}$ and/or $Fe^{3+}$ salt, is carried out at a temperature and length of time sufficient to penetrate the hair, typically at 10 to 50° C., preferred at 20 to 50° C., even more preferred room temperature (25°), for 5 to 120 min, preferred 5 to 60 min, even more preferred 10 to 40 min, the step of drying the treated hair by applying heat with T>150° C., preferably a hot ironing step, is carried out at temperatures ranging from 1500° C. to about 235° C., more preferred from 180° C. to about 225° C., even more preferred from 190° C. to about 215° C., and where typically 2 to 10 times of hot ironing are applied.

The hair treatment process according to the invention is preferably suitable for strengthening of hair, for hair coloring, for hair color retention, for shaping of hair, i.e. the curling and straightening of hair, for hair conditioning.

Most preferably the hair treatment process according to the invention, comprises the application of the aqueous compositions or hair treatment compositions according to the invention to dyed hair.

The above described aqueous compositions according to the invention are particularly useful for strengthening of hair, for hair color retention, for hair color enhancement, for hair color protection, for shaping of hair, i.e. the curling and straightening of hair, for hair conditioning, for hair smoothening or softening, for hair straightening, for improving manageability of the hair, in particular for improving the combability of the hair. They can provide in particular benefits with respect to an improved durability of artificial colors on hair, and have additionally a hair strengthening and shaping effect as well as a conditioning effect.

The aqueous compositions according to the invention can be formulated into a form typical for hair treatment compositions. Preferred are topical hair care or treatment compositions, e.g. hair tonics, conditioners, hair-care preparations, e.g. pre-treatment preparations, styling creams, styling gels, pomades, hair rinses, treatment packs, intensive hair treatments e. g. leave-on and rinse-off deep conditioners, hair-structuring preparations, e.g. hair-waving preparations for permanent waves (hot wave, mild wave, cold wave), hair-straightening preparations, liquid hair-setting preparations, hair foams, hair serums, hair sprays, bleaching preparations, e g. hydrogen peroxide solutions, lightening shampoos, bleaching creams, bleaching powders, bleaching pastes or oils, temporary, semi-permanent or permanent hair colorants, preparations containing self-oxidizing dyes, or natural hair colorants, such as henna or chamomile. Based on the application the hair care preparations may be in particular in the form of a (aerosol) spray, (aerosol) foam, gel, gel spray, cream, lotion, liquid, serum or a wax, mousse, shampoo, such as pearl shampoo, anti-frizz shampoo etc.

The aqueous compositions according to the invention can be used as leave-on or rinse-off hair treatment compositions.

EXAMPLES (All percentages are weight (wt) percentages unless indicated otherwise).

Example 1

Synthesis of a Dihydroxy Benzoic Acid Derivative (Component A))

120.52 g propylene glycol mono methyl ether, 18.14 g (0.118 mol —COOH) 3,4-dihydroxy benzoic acid, 0.5 g triethylamine and 33.51 g (0.107 mol epoxy groups) of an epoxy functionalized silicone of the structure

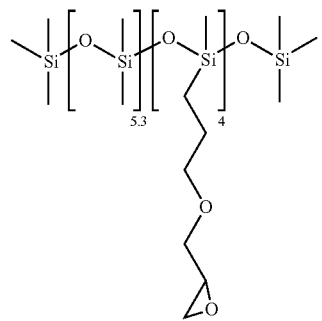

were mixed at room temperature and heated to 120° C. for 22 hrs. The conversion on epoxy groups was 100% (1H-NMR).

The solvent was removed at 65° C./20 mmHg. Afterwards, the material was washed twice with 25 ml n-hexane. The solvent was removed at 65° C./20 mmHg. A brownish opaque product of the structure

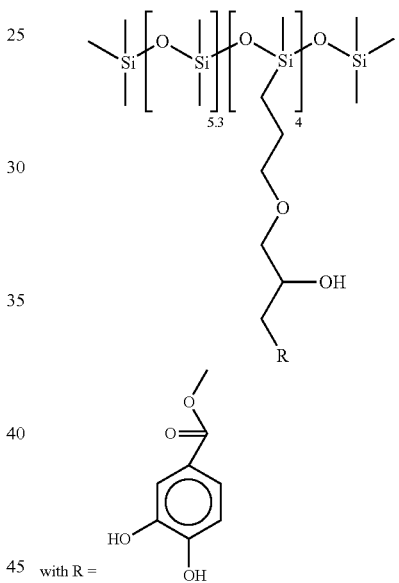

was obtained.

Aqueous Composition of the Component A) (Comparison)

A solution of 0.5 g of the product according to example 1 in 9.5 g deionized water is turbid.

According to WO2016046178, Example 9, Formulation F1, 0.5 g of the product according to example 1 were mixed with 9 g deionized water and 0.5 g of an 25% active aqueous $NH_3$ solution. A transparent brownish solution was formed. This solution turns turbid upon storage at RT after two days.

Example 2

Synthesis of a Trihydroxy Benzoic Acid Derivative (Component A))

120.78 g propylene glycol mono methyl ether, 19.36 g (0.113 mol —COOH) 3,4,5-trihydroxy benzoic acid, 0.32 g triethylamine and 32.40 g (0.103 mol epoxy groups) of an epoxy functionalized silicone of the structure

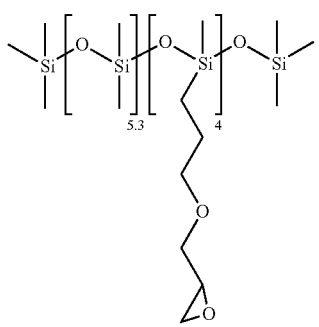

were mixed at room temperature and heated to 120° C. for 26 hrs. The conversion on epoxy groups was 98% (1H-NMR).

The solvent was removed at 65° C./20 mmHg. Afterwards, the material was washed twice with 25 ml n-hexane. The solvent was removed at 65° C./20 mmHg. A brownish opaque product of the structure

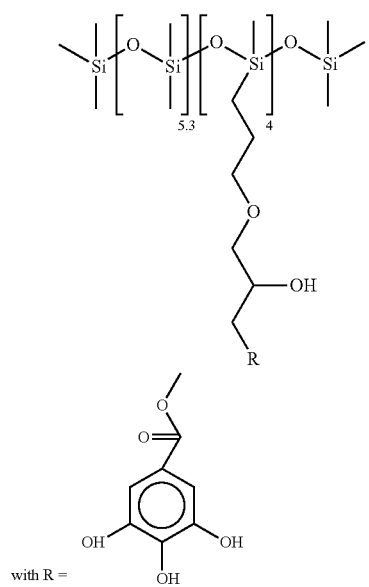

was obtained.

Aqueous Composition of Component A) (Comparison)

A solution of 0.5 g of the product according to example 2 in 9.5 g deionized water is turbid.

According to WO2016046178, Example 9, Formulation F2, 0.5 g of the product according to example 2 were mixed with 9 g deionized water and 0.5 g of an 25 wt-% active aqueous $NH_3$ solution. A transparent brownish solution was formed. This solution turns turbid upon storage at RT after two days.

Example 3A (Component A) and C) (Starting Material))

Synthesis of a Trihydroxy Benzoic Acid Derivative in Propylene Glycol Mono Methyl Ether 1260 g propylene glycol mono methyl ether, 10.8 g triethylamine and 214.89 g (1.263 mol —COOH) 3,4,5-trihydroxy benzoic acid are mixed under $N_2$ at room temperature and heated to 106° C. 344.65 g (1.148 mol epoxy groups) of an epoxy functionalized silicone of the structure

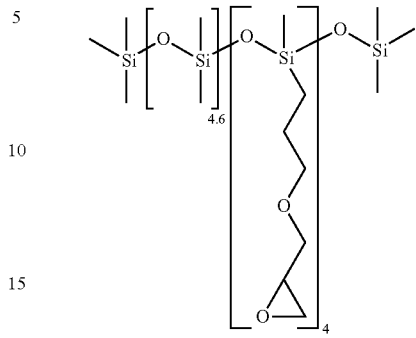

were added within 30 minutes. The temperature increased from 106° C. to 120° C. The temperature is maintained between 114 and 120° C. for 19 hrs. The conversion on epoxy groups was 100% (1H-NMR).

The polymer has the approximate structure

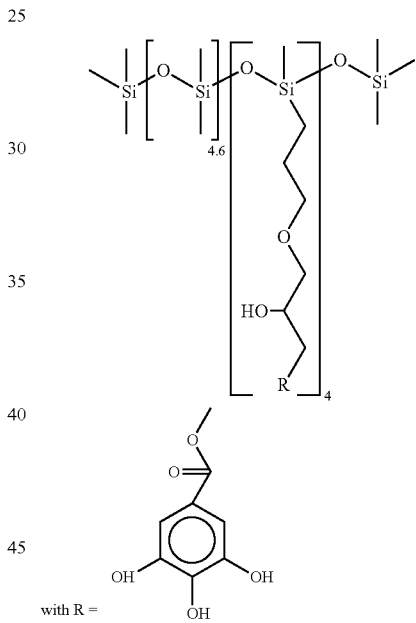

A brownish 30% active polymer solution in propylene glycol mono methyl ether was obtained which can used without any further purification (example 3A).

Example 3B (Component A) and C) (Starting Material))

Synthesis of a Trihydroxy Benzoic Acid Derivative in DPG 100 g of the 30% active polymer solution in propylene glycol mono methyl ether according to example 3A were mixed with 70 g dipropylene glycol. The low boiling propylene glycol mono methyl ether was removed at 40° C./20 mmHg.

A brownish polymer solution in dipropylene glycol was obtained which can be used without any further purification (example 3B).

Example 4 (Component A) and C) (Starting Material))

Synthesis of a Trihydroxy Benzoic Acid Derivative 52.33 g propylene glycol mono methyl ether, 7.43 g (0.0437 mol —COOH) 3,4,5-trihydroxy benzoic acid, 0.22 g triethylamine and 15.19 g (0.0397 mol epoxy groups) of an epoxy functionalized silicone of the structure

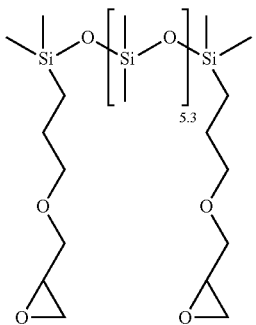

were mixed at room temperature and heated to 120° C. for 16 hrs. The conversion on epoxy groups was 100% (1H-NMR). A transparent brownish polymer solution was obtained (Example 4). The polymer has the approximate structure

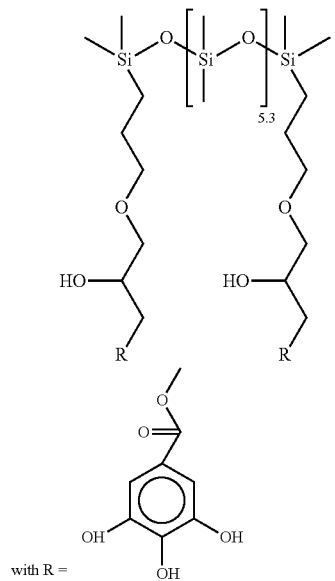

Example 5 (Component A) and C) (Starting Material))

Synthesis of a Difunctional Trihydroxy Benzoic Acid and Glyoxylic Acid Derivative 58.63 g propylene glycol mono methyl ether, 4.60 g (0.027 mol —COOH) 3,4,5-trihydroxy benzoic acid, 1.65 g (0.018 mol —COOH) glyoxylic acid monohydrate, 0.5 g triethylamine and 19.35 g (0.045 mol epoxy groups) of an epoxy functionalized silicone of the structure

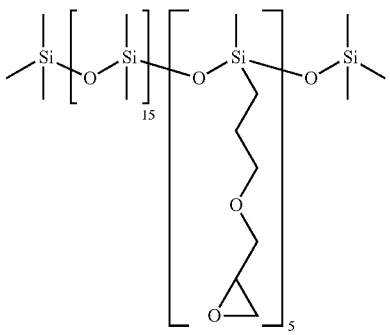

were mixed at room temperature and heated to 100° C. for 55 hrs. The conversion on epoxy groups was 96% (1H-NMR).

A transparent brownish polymer solution was obtained (Example 5). The polymer has the approximate structure

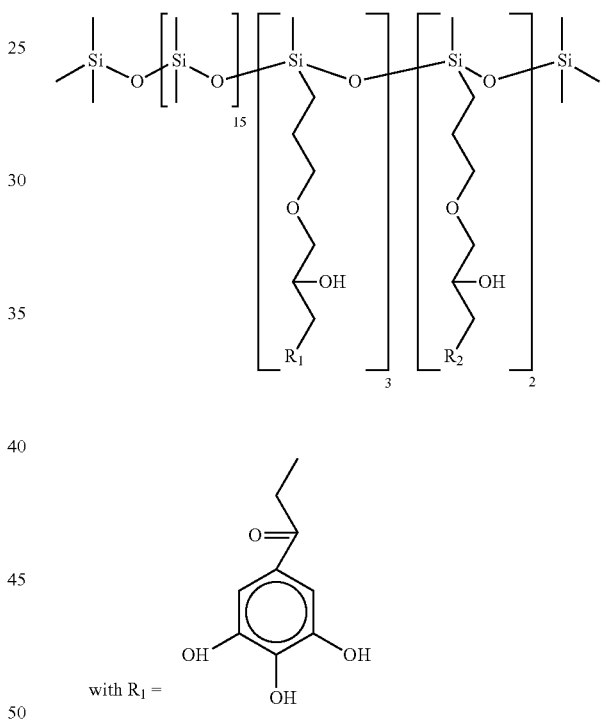

and $R_2$=—OC(O)C(O)H was obtained.

Example 6 (Component A) and C) (Starting Material))

Synthesis of a Difunctional Trihydroxy Benzoic Acid and Succinic Amide Derivative 60.8 g propylene glycol mono methyl ether, 4.60 g (0.027 mol —COOH) 3,4,5-trihydroxy benzoic acid, 2.11 g (0.018 mol —COOH) succinic acid monoamide, 0.5 g triethylamine and 19.35 g (0.045 mol epoxy groups) of an epoxy functionalized silicone of the structure

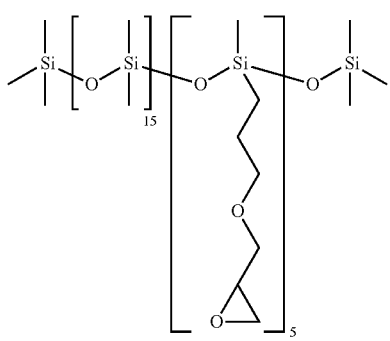

were mixed at room temperature and heated to 100° C. for 34 hrs. The conversion on epoxy groups was 98% (1H-NMR).

A transparent dark brownish polymer solution was obtained (Example 6). The polymer has the approximate structure

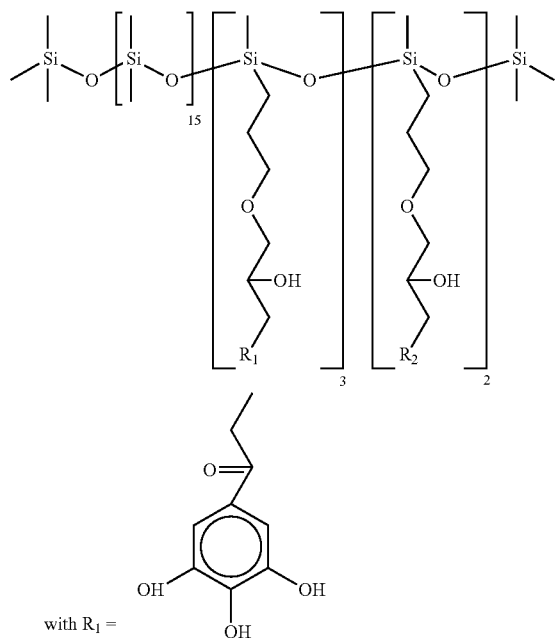

and $R_2 = -OC(O)CH_2CH_2C(O)NH_2$ was obtained.

Measurement Methods:

Test Method for Measuring Color and Color Retention of Hair Dyes

The test method for evaluation of the color retention is described in detail in US 201110219552 A1. The method determines the change in hair color (Delta E) before and after washing the hair. The color changes were determined by measuring the Hunter L, a and b values on a HunterLab colorimeter before and after washing the color treated hair tress.

The meaning of L, a, b was elaborated in "Practical Modern Hair Science" Trefor Evans and R. Randall Wichett, Alluredbooks, Carol Stream, Ill., 2012. The L value measures the lightness from L=0 (black) to L=100 (white). The color is measured by a from negative value (green) to positive value (red) and b from negative value (blue) to positive value (yellow). For example, a medium blonde has an L, a, b value of L=49, a=12, b=26 and a medium auburn has an L, a, b value of L=26, a=13, b=12.

Delta E was calculated using the following equation to evaluate color change before and after washes.

Delta $E_w = ((L_t - L_0)^2 + (a_t - a_0)^2 + (b_t - b_0)^2)^{1/2}$

Where $L_0$, $a_0$, $b_0$, (initial color parameters) and $L_t$, $a_t$, $b_t$ (color parameters after washing) are measured Hunter L, a, b color parameters. The larger value of Delta E the greater change of color, so smaller Delta E is desired because it indicates less color loss after washing.

Similarly, color enhancement was calculated using the following equation to evaluate initial color depth increase with treatment.

Delta $E_e = ((L_2 - L_1)^2 + (a_2 - a_1)^2 + (b_2 - b_1)^2)^{1/2}$

Where $L_2$, $a_2$, $b_2$, (color parameters for treated colored hair) and $L_1$, $a_1$, $b_1$ (color parameters for untreated colored hair) are measured without washing. Here a larger Delta E is desired because it means more initial color enhancement.

Hair Fiber Mechanical Properties

The mechanical properties were obtained by single fiber tensile tests using a sample of 50 fibers and a Diastron automated tensile tester. Hair Fibers were immersed in water for measuring the wet young modulus and the wet break strength.

The formulations according to the invention are labeled F1 to F19.

The non-inventive formulations are labeled CF1 to CF5.

Example 7: Ready to Dilute Composition (Concentrate)

|  | F1 | F2 | CF1 |
|---|---|---|---|
| Cetyltrimonium chloride B1) | 20 | 20 |  |
| Polyorganosiloxane A) example 3A | 10 | 10 | 10 |
| ratio B1)/A) | 2 | 2 | 0 |
| Propylene glycol mono methyl ether C) | 23 |  | 23 |
| Dipropylene glycol C) |  | 23 |  |
| ratio C)/A) | 2.3 | 2.3 | 4.6 |
| water | 47 | 47 | 47 |
| pH | 3.6 | 4.3 | ?3.5 |
| Appearance | clear | clear | turbid |
| Stability at RT | >40 d | >40 d | unstable |

The example shows that a concentrated aqueous composition of the invention can be prepared, which is clear and stable for a long time and can be delivered to customers for the preparation of formulations for the treatment of hair.

Example 8: Substrate Treatment Compositions

TABLE 1

| compositions (wt-%) | | | | | | | | | | | |
|---|---|---|---|---|---|---|---|---|---|---|---|
|  | F3 | F4 | F5 | F6 | F7 | F8 | F8A | CF2 | CF3 | CF4 | CF5 |
| Cetyltrimonium chloride B1) | 3 | 1.5 | 0.75 | 0.5 | 0.3 | 0.16 | 3 | 0.08 | 0 | 0 | 0 |

TABLE 1-continued

| compositions (wt-%) | | | | | | | | | | | |
|---|---|---|---|---|---|---|---|---|---|---|---|
| | F3 | F4 | F5 | F6 | F7 | F8 | F8A | CF2 | CF3 | CF4 | CF5 |
| Polyorganosiloxane A) example 3A | 1.5 | 1.5 | 1.5 | 1.5 | 1.5 | 1.5 | 1.5 | 1.5 | 1.5 | | |
| Polyorganosiloxane A) example 2 | | | | | | | | | | 5 | 5 |
| ratio B1)/A) | 2 | 1 | 0.5 | 0.33 | 0.2 | 0.1 | 2 | 0.05 | 0 | 0 | 0 |
| Propylene glycol mono methyl ether C) | 3.5 | 3.5 | 3.5 | 3.5 | 3.5 | 3.5 | 0 | 3.5 | 3.5 | 0 | 0 |
| ratio C)/A) | 2.3 | 2.3 | 2.3 | 2.3 | 2.3 | 2.3 | | 2.3 | 2.3 | 0 | 0 |
| $NH_3$ 25% in water | | | | | | | | | | | 5 |
| Water | Qs to 100 | Qs to 100 | Qs to 100 | Qs to 100 | Qs to 100 | Qs to 100 | QS to 100 | Qs to 100 | Qs to 100 | Qs to 100 | QS to 100 |
| NaOH 1% | qs to pH 3 | qs to pH 3 | qs to pH 3 | qs to pH 3 | qs to pH 3 | qs to pH 3 | qs to pH 3 | qs to pH 3 | qs to pH 3 | qs to pH 3 | <8 |
| Appearance | clear | clear | clear | clear | Translucent | Translucent | clear | turbid | turbid | turbid | clear |
| Stability at RT | >40 d | >40 d | >40 d | >40 d | >40 d | >40 d | >40 d | 2 phases | 2 phases | 2 phases | 2 d, then 2 phases |

The example shows that an aqueous composition of the invention can be prepared, which is clear or translucent and stable for a long time.

Example 9: Substrate Treatment Compositions

TABLE 2

| Composition (wt-%) | | | | | |
|---|---|---|---|---|---|
| | F9 | CF 6 | CF7 | CF8 | CF9 |
| Cocoamidopropylbetaine | 1 | | | | |
| Sodium Laureth Sulfate B2) | 7 | 1.25 | 0.78 | | 0.08 |
| Cocoglucoside | | | | 5 | |
| Polyorganosiloxane A) example 3A | 1.5 | 1.5 | 1.5 | 1.5 | 1.5 |
| ratio B2)/A) | 4.7 | 0.8 | 0.52 | 0 | 0.05 |
| Propylene glycol mono methyl ether C) | 3.5 | 3.5 | 3.5 | 3.5 | 3.5 |
| ratio C)/A) | 2.3 | 2.3 | 2.3 | 2.3 | 2.3 |
| Water | q.s to 100 | q.s to 100 | q.s to 100 | q.s to 100 | q.s to 100 |
| Citric acid 10% | q.s to pH 4.5 | | | | |
| NaOH 10% | | q.s. to pH 8 | q.s. to pH 8 | q.s. to pH 8 | q.s. to pH 8 |
| Appearance >2 days | Clear light amber | Clear dark amber | Clear dark amber | Clear dark amber | Turbid dark amber |
| Stability at RT | >40 d | >40 d | >40 d | >40 d | 2 phases |

The examples show that the aqueous compositions of the invention surprisingly form stable formulations at rather low level of the cationic surfactant at low pH. It is assumed that under acidic conditions the oxidation of the polyorganosiloxane A) is slowed down as evidenced by the brighter appearance of the aqueous compositions.

Example 10: Hair Treatment Compositions for Hair Coloring

TABLE 3

| compositions (wt-%) | | | | | |
|---|---|---|---|---|---|
| | F10 | F 11 | F12 | F13 | F14 |
| Cetyltrimonium chloride B1) (30 wt-%) | 3 | 3 | 3 | 3 | 3 |
| Polyorganosiloxane A) example 3A | 1.5 | 1.5 | 1.5 | 1.5 | 1.5 |
| ratio B1)/A) | 2 | 2 | 2 | 2 | 2 |
| Ferrous sulfate | 0.05 | 0.1 | 0.25 | 0.5 | 0.5 |
| Maltobionic acid | | | | | 1.2 |

TABLE 3-continued

| | compositions (wt-%) | | | | |
|---|---|---|---|---|---|
| | F10 | F 11 | F12 | F13 | F14 |
| Propylene glycol mono methyl ether C) | 3.5 | 3.5 | 3.5 | 3.5 | 3.5 |
| ratio C)/A) | 2.3 | 2.3 | 2.3 | 2.3 | 2.3 |
| NaOH 1% | Qs to pH 3 | Qs to pH 3 | Qs to pH 3 | Qs to pH 3 | Qs to pH 3 |
| Water | q.s to 100 | q.s to 100 | q.s to 100 | q.s to 100 | q.s to 100 |
| Stability at RT | >40 d | >40 d | >40 d | >40 d | >40 d |

In Example formulations F10-14, Cetyltrimonium chloride was an aqueous 30 wt.-% solution.

The solution of Polyorganosiloxane A) in propylene glycol mono methyl ether C) was added to the cetyltrimonium solution and mixed with a vortex mixer to obtain a clear solution.

The ferrous sulfate was first diluted in water to form a 5% solution, and then added to the cationic surfactant/polyorganosiloxane A).

In these examples the composition contain the galloyl-substituted polyorganosiloxanes and iron salts. It is assumed that they form a colored complex which is stabilized by the surfactant. The composition has a dark purple color and can slightly darken the hair. Furthermore it is assumed that metal salts also act as crosslinking chelating cations linking different polyorganosiloxane molecules or polyorganosiloxane molecules with the keratinous substrates, thereby increasing substantivity of the polyorganosiloxane and sealing the hair surface against color washing-off. Maltobionic acid is assumed to maintain the iron cations at higher pH.

Example 11: Application on Dyed Hair (Oxidative Dye)

6 g single bleached hair tress from Hair International importers was dyed with Feria 66 red Dye from L'Oréal according to the instruction. After dyeing the tress was divided in two halves. One half was treated with the composition F14 with a sponge brush and a loading of 1.3 g/g of hair. The composition was left on the hair for 5 minutes. The hair was rinsed for 1 min, washed with 10% SLES, and rinsed again under tap water. The other half tress was the comparative tress and was simply washed with 10% SLES (sodium laureth sulfate used in all examples was with 2 EO), similarly to the example tress. Multiple washes were performed. The hair color was measured before the washes, and after multiple washes.

The hair color was measured with Colorquest by measuring L, a and b values and calculating the delta E value. The smaller the value of ΔE (i.e. lowest color change from the original color), the better the color retention is.

TABLE 4

| | Color retention test | | |
|---|---|---|---|
| | ΔE after 3 washes | ΔE after 6 washes | ΔE after 9 washes |
| Example Tress | 1.1 | 1.5 | 3.1 |
| Comparative Tress | 3.4 | 5 | 5.2 |

Table 4 shows that the example tress retains its color better (lower ΔE values) than the untreated comparative tress.

Example 12: Strengthening of Dyed Hair (Oxidative Dye)

6 g single bleached hair tress from Hair International importers was dyed with Feria 66 red Dye from L'Oréal according to the instruction. After dyeing the tress was divided in two halves. One half was treated with the composition F14 with a sponge brush and a loading of 1.3 g/g of hair. The composition was left on the hair for 5 minutes. The hair was rinsed for 1 min, washed with 10% SLES (sodium laureth sulfate), and rinsed again under tap water. The other half tress was the comparative tress and was simply washed with 10% SLES, similarly to the example tress.

TABLE 5

| | Single fiber tensile test results | |
|---|---|---|
| | Wet elasticity (Pa) | Break strength (wet) Gram/square micron |
| Example tress | 1.14E+09 | 1.43E−02 |
| Comparative tress | 9.66E+08 | 1.32E−02 |

The example shows the hair strengthening effect of the aqueous compositions of the invention. It is assumed that the metal salt can chelate some portions of keratin and also the galloyl silicone A), which causes hair strengthening. As the galloyl silicone A)/metal complex is also colored, it also colors the hair. Again maltobionic acid helps to keep the iron salt stable at higher pH.

Example 13: Application on Dyed Hair (Oxidative Dye) after Color Fading

An European single bleached hair tress was dyed with a burgundy color oxidative dye (Estel, Love Intense, 7/5) according to the manufacturer instruction. After the dyeing, the hair tress was split in two halves. To obtain color fading, the tress was immersed in an agitated 2.5% SLES bath at 40° C. for 5 min.

One half of the tress was soaked in the ink-composition example F14 for 20 minutes. It was then rinsed under tap water abundantly and dried for measurement. It was then subjected to 6 wash cycles. The other half was only subjected to the 6 wash cycles.

After dyeing the tress has a deep burgundy color. After fading (F) the hair became lighter (higher L value) and shifts toward an orange color (higher b value). With the ink treatment (F+I), the hair becomes darker and regains its burgundy color (low L and b values). The restored burgundy color (F+I+W) is retained after 6 washes.

| | Tress ID | L | b |
|---|---|---|---|
| Initial color | I | 20.39 | 4.99 |
| Color after the fading process (F) | F | 23.69 | 7.87 |
| Color after the ink treatment (F + I) | F + I | 19.77 | 3.78 |
| Color after the fading process and 6 additional wash (F + W) | F + W | 25 | 8.02 |
| Color after the ink and 6 additional wash (F + I + W) | F + I + W | 22.22 | 4.76 |

Example 14: Application on Dyed Hair with Acid Dye for Adjustment of Red Shad The single bleached hair (4 g) was dyed with a red acid dye (anthocyan, color) according to the protocol indicated on the product box. The hair was then treated with 3.5 g of the-composition F13 and left for 20 min in contact with the composition F13. The hair was rinsed under tap water and dried. The hair with acid dye is bright red and become a darker red color after the application of the composition.

| | L | a | b |
|---|---|---|---|
| Initial color | 27.79 | 36.24 | 10.62 |
| Color after the treatment with composition F13 (F) | 24.00 | 26.60 | 8.15 |

Example 15: A Two Steps Application to Color Bleached Hair

A Dry Single bleached hair tress from Hair International (light blond color) was saturated with the composition F3 shown in Table 1. The solution was massaged into the hair and left in the hair for 15 minutes. A solution containing 3% cetyl trimonium chloride and 0.5% ferrous sulfate was then applied and massaged into the hair. The metal solution was left into the soaked hair for another 15 min. The hair was then rinsed abundantly under tap water and dried.

The hair becomes dark blond.

| | L | a | b |
|---|---|---|---|
| initial color | 43.07 | 5.09 | 14.02 |
| After two step application | 28.39 | 2.58 | 5.51 |
| After 3 washes | 30.86 | 2.54 | 5.84 |

The two solutions are almost not colored, but they become more intense colored when they come into contact, presumably because the galloyl silicone A) and the metal salt form a complex together. With the two steps process, the galloyl silicone A) penetrates the hair first and then the metal salt penetrates the hair and forms a colored complex. With the one step process using compositions F10-14 for example, the complex is already formed and may not penetrate the hair very well, leading to a more faint color of the hair.

Example 16: Clear Hair Shampoo Composition

| | F15 | F18 |
|---|---|---|
| Cocoamidopropylbetaine | 1.9 | 1.9 |
| Sodium Laureth Sulfate B2) | 13.3 | 13.3 |
| Sodium chloride | 1.4 | 1.4 |
| Polyorganosiloxane A) example 3A | 1.5 | 1.5 |
| ratio B2)/A) | 8.9 | 8.9 |
| Tannic acid* | | 1.5 |
| Propylene glycol mono methyl ether C) | 3.5 | 3.5 |
| ratio C)/A) | 2.3 | 2.3 |
| water | q.s to 100 | q.s to 100 |
| pH | | 4.7 |
| Appearance | clear | clear |
| Stability at RT | >40 d | >40 d |

(*Tannic acid was Tannal from Ajinomoto; color enhancement additive)

Example 17: Hair Care Compositions

| | F17 | F18 |
|---|---|---|
| Cetearyl alcohol | 4 | |
| Cetyltrimonium chloride B1) | 3 | 3 |
| cellulose | 1 | 1 |
| Polyorganosiloxane A) example 3A | 1.5 | 1.5 |
| ratio B1)/A) | 2 | 2 |
| Propylene glycol mono methyl ether C) | 3.5 | 3.5 |
| ratio C)/A) | 2.3 | 2.3 |
| water | q.s to 100 | q.s to 100 |
| pH | 3-4 | 3-4 |
| Stability at RT | >40 d | >40 d |

Example 18: Two Steps Hair Coloration and Strengthening Using a Shampoo

Platinum bleached hair tress (4 gram) from hair international was shampooed with 1 g of the example composition F15 of Example 16. The hair soaked with the shampoo for 5 min and rinsed. Excess of liquid was squeezed out of the hair. An amount of 1 gram of a solution containing 4.2% ferrous sulfate and 10% of maltobionic acid adjusted to pH 6 and 1 gram of a pH 8 tris buffer was spread on the wet hair. The hair soaked with the metal solution for a total of 10 min and rinsed with tap water and dried. The 2 steps shampoo process was repeated twice giving the hair a light brown coloration. The tensile tests (50 fibers) showed that wet tensile elasticity of the colored hair was improved by about 20% relative to the initial hair before dyeing.

Example 19: Color Protection Shampoo for Dyed Hair

The following shampoo formulations were made:

| Chemical Name | Shampoo CF10 wt % | Shampoo F19 % | Shampoo CF11 % | Shampoo CF12 % |
|---|---|---|---|---|
| SLES-2 (Sodium Laureth Sulfate with 2 EO) B2) | 14 | 14 | 14 | 14 |
| CapB (Cocamidopropyl Betaine) | 2 | 2 | 2 | 2 |
| Polyorganosiloxane A) from example 3A | — | 1.5 | — | — |
| ratio B2)/A) | — | 9.3 | — | — |
| Propylene glycol mono methyl ether C) | — | 3.5 | — | 3.5 |

-continued

| Chemical Name | Shampoo CF10 wt % | Shampoo F19 % | Shampoo CF11 % | Shampoo CF12 % |
|---|---|---|---|---|
| ratio C)/A) | 0 | 2.3 | — | — |
| Olaplex | — | — | 7.1 | — |
| Maleic acid | — | — | — | 0.15 |
| NaCl | 1.5 | 1.5 | 1.5 | 1.5 |
| pH | ~4.5 | ~4.5 | ~4.5 | ~4.5 |
| Water | q.s. to 100 | q.s. to 100 | q.s. to 100 | q.s. to 100 |

Single bleached European hair was dyed with Estel Love Intense 7/5 Rubin (Estel) following the standard dyeing procedure given for Estel 7/5. Afterwards, the clear shampoo formulations F19, CF10. CF11, CF12 were applied to the dyed hair at a level of 1 g per 4 g tress by rubbing in. The hair was rinsed off with water (41° C.) for 2 minutes and dried under bonnet. In total, the hair was washed, dried and analyzed six times. The hair color was measured before the shampoo treatment and after each single shampoo treatment.

Table 2 shows the color loss Delta E, which quantifies the color loss, after six washing cycle.

TABLE 2

Hair color change after 6 shampoo wash cycles:

| Shampoo treatment | ΔE color change after 6 shampoo wash cycles |
|---|---|
| Example F19 | 0.5 |
| Comparative CF10 | 3.8 |
| Comparative CF11 | 6 |
| Comparative CF12 | 5.2 |

The color change of the tress washed with example F19 is much lower than the color change of the tresses washed with the comparative shampoos (CF10-CF12). The shampoo Example F19 shows a much lower color loss compared to the other comparative treatments. The red component remains almost unchanged after six washing cycles while the other treatments show a steady increase of the color loss.

Example 20: Rinse Off Conditioner

| Part | Chemical Name | wt-% |
|---|---|---|
| A | Water | q.s. to 100 |
|   | Lactic Acid | 0.6 |
| B | Amidet APA-22 (Behenamidopropyl Dimethylamine) from Kao Corporation B1) | 2.2 |
| C | Kalcol 6850 (Cetostearyl alcohol) from Kao Corporation | 4.4 |
| D | Polyorganosiloxane Example 3A A) | 1.5 |
| D | Propylene glycol mono methyl ether C) | 3.5 |
| ratio B1)/A) | | 1.47 |
| ratio C)/A) | | 2.3 |
| pH | | 3.5 |

1. Part A. Lactic acid and water were mixed and heated to 80° C.
2. Part B was added to part A and the mixture stirred (speed?) for 1-3 hours at 80° C. to provide a homogeneous formulation.
3. Part C was added to the mixture of A and B and stirred at 80° C. for 0.5 to 1 hour until Part C was completely molten and a homogeneous mixture was obtained.
4. The heating source was removed while stirring continued until room temperature was reached.
5. Part D was added to the mixture consisting of A + B + C and stirring continued until a homogeneous mixture was reached.

Example 21: Pearlescent Shampoo

| Part | Component | wt % |
|---|---|---|
| A | Sodium Laureth Sulfate B2) | 12 |
|   | Cocamidopropyl Betaine | 3 |
| B | Ethylene Glycol Distearate | 1 |
|   | Water | 10 |
| C | Cocamide Monoethanolamide | 1 |
|   | Water | 10 |
| D | Polyquaternium-6 | 0.06 |
|   | ACULYN™ 38 from the Dow Chemical Company (10 wt-% active) | 3 |
| E | Polyorganosiloxane A) (Example 3B) | 1.5 |
|   | Dipropylene glycol C) | 3.5 |
| F | Water | q.s. to 100 |
| ratio B2)/A) | | 8 |
| ratio C)/A) | | 2.3 |
| pH | | 4.5 |

Part A: The components of part A were mixed with an overhead mechanical stirrer at 600 rpm for 10 minutes.
Part B: 1 g ethylene glycol distearate and 10 g water were mixed with a magnetic stirrer at 200 rpm for 15 minutes.
Part C: 1 g cocamide monoethanolamide and 10 g water were mixed with a magnetic stirrer at 200 rpm for 15 minutes.
The components of part D were added to part A and stirred with an overhead mechanical stirrer at 600 rpm for 10 minutes. A mixture A + D was obtained.
Part B was added to the mixture A + D and stirred for 10 minutes at 600 rpm with a mechanical stirrer. Mixture A + D + B was obtained.
Part C was added to the mixture A + D + B and stirred for 10 minutes at 600 rpm with a mechanical stirrer. Mixture A + D + B + C was obtained.
Part E was added to the mixture A + D + B + C and stirred for 15 minutes at 600 rpm with a mechanical stirrer. Mixture A + D + B + C + E was obtained.
Part F was added last to the mixture A + D + B + C + E and the mixture stirred for 15 minutes at 600 rpm with a mechanical stirrer.

Example 22: Sulfate Free Shampoo

| Part | Component | wt % |
|---|---|---|
| A | Sodium Lauryl Sulfoacetate + Disodium Laureth Sulfosuccinate (wt-ratio 1:1 - component B2)) | 10.6 |
|   | Cetyl Betaine | 3.3 |
| B | Cocamide Monoethanolamide | 1.5 |
|   | Wafer | 10 |
| C | Hydroxypropyl Methylcellulose | 1.5 |
|   | Water | 10 |
| D | Ethylene Glycol Distearate | 1.5 |
|   | Water | 10 |
| E | Polyquaternium-10 | 0.15 |
| F | Polyorganosiloxane A) (Example 3A) | 1.5 |
|   | Propylene glycol mono methyl ether C) | 3.5 |
| G | Water | q.s. to 100 |
| ratio B2)/A) | | 7.1 |
| ratio C)/A) | | 2.3 |
| pH | | 4.5 |

Part A: The components of part A were mixed with an overhead mechanical stirrer at 600 rpm for 10 minutes.
Part B: 1.5 g cocamide monoethanolamide was mixed with 10 g water (45° C.) with a magnetic stirrer at 200 rpm for 30 minutes.
Part C: 1.5 g hydroxypropyl methylcellulose powder was slowly added to 10 g water (45° C.) and stirred with a magnetic stirrer at 200 rpm for 30 minutes.
Part D: 1.5 g ethylene glycol distearate powder was slowly added to 10 g water (45° C.) and stirred with a magnetic stirrer at 200 rpm for 30 minutes.
Part B was slowly added to part A with mechanical stirring at 600 rpm for 5 minutes. Mixture A + B was obtained.
Part C was slowly added to part A + B with mechanical stirring at 600 rpm for 5 minutes. Mixture A + B + C was obtained.
Part D was slowly added to part A + B + C with mechanical stirring at 600 rpm for 5 minutes. Mixture A + B + C + D was obtained.
Part E was added to part A + B + C + D with mechanical stirring at 600 rpm for 10 minutes. Mixture A + B + C + D + E was obtained.
Part F was added to the mixture A + B + C + D + E and mechanically stirred for 15 minutes at 600 rpm.
Finally, Part G was added and the mixture stirred at 600 rpm for 30 minutes.

The invention claimed is:
1. An aqueous composition for hair treatment, comprising at least one polyorganosiloxane A) having an average number of 2 to 1000 siloxy units selected from the siloxy groups of the formulas:

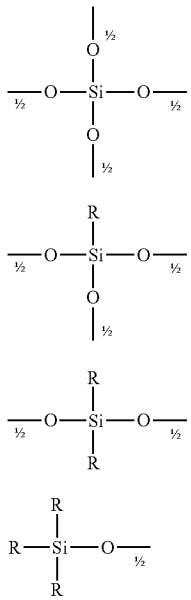

(Q)
(T)
(D)
(M)

wherein
each R is independently selected from $R^1$ and at least one group $R^{F1}$, wherein
$R^1$ is selected from organic groups bound to the silicon atoms by a carbon atom, and two groups $R^1$ may form a bridging group between two silicone atoms, and
$R^{F1}$ is selected from organic groups different from $R^1$ and is bound to the silicon atoms by a carbon atom, which contain at least one functional group F1 selected from the group consisting of di- and trihydroxy-substituted aromatic groups,
and
at least one surfactant B) selected from the group consisting of cationic surfactants B1) and anionic surfactants B2),
wherein the aqueous composition has a pH at 20° C. of from 2 to 5, wherein the aqueous composition shows no phase separation for a period of 0 to 40 days at a temperature of about 25° C., wherein the weight ratio of cationic surfactant B1) to polyorganosiloxane A) is 0.1 to 5, and wherein the weight ratio of anionic surfactant B2) to polyorganosiloxane A) is 3 to 11.5.

2. The aqueous composition according to claim 1, comprising 0.01 to 40 wt-% of the polyorganosiloxane A) based on the total weight of the aqueous composition.

3. The aqueous composition according to claim 1, comprising 0.01 to 7 wt-% of the polyorganosiloxane A) based on the total weight of the aqueous composition.

4. The aqueous composition according to claim 1, comprising 0.01 to 30 wt-% of the surfactant B) based on the total weight of the aqueous composition.

5. The aqueous composition according to claim 1, wherein the surfactant B) is a cationic surfactant B1).

6. The aqueous composition according to claim 1, wherein the surfactant B) is an anionic surfactant B2).

7. The aqueous composition according to claim 1 which further comprises at least one non-aqueous diluent C).

8. The aqueous composition according to claim 1, wherein the cationic surfactant B1) is selected from primary, secondary, or tertiary amine compounds having up to 50 carbon atoms and salts thereof, amido amine compounds having up to 50 carbon atoms and salts thereof, and quaternary ammonium compounds having up to 50 carbon atoms.

9. The aqueous composition according to claim 1, wherein the anionic surfactant B2) is selected from the group consisting of organic sulfates, organic sulfonates, organic phosphates, organic phosphonates, and organic carboxylates.

10. The aqueous composition according to claim 1, wherein the polyorganosiloxane A) in addition to $R^{F1}$ has at least one further functional organic group $R^{F2}$ different from $R^1$ and $R^{F1}$, which is bound to the silicon atoms by a carbon atom and which comprises at least one functional group F2, selected from the group consisting of:
alkoxy silyl group,
amino group, or azetidine group,
ammonium group, or azetidinium group,
phosphonium group,
epoxy group,
carbonate group,
urethane group,
isocyanate group, or blocked isocyanate group,
urea group,
amido group, or carbamoyl group,
aldehyde group,
methylol group,
acetale or half acetale group,
Schiff-Base or enamine group,
zwitterionic group,
carboxylic acid or carboxylate group,
sulfonic acid or sulfonate group,
sulfuric acid half ester or sulfate group,
phosphoric acid ester or phosphate group,
phosphoric acid ester or phosphonate group,
phosphorous acid ester or phosphite group,
xanthogenate/xanthogenate ester group,
thiosulfato group,
a monohydroxy-substituted aromatic group,
mercapto group,
saccharide group,
polyether group with up to 60 carbon atoms,
thio ester,
thio ether group, and
combinations of said functional groups.

11. The aqueous composition according to claim 1, wherein the organic radicals $R^1$ are selected from the group consisting of straight-chain, cyclic or branched, saturated, unsaturated or aromatic hydrocarbon radicals which have up to 100 carbon atoms which optionally contain one or more groups selected from —O—, and which are optionally substituted by one more groups selected from the group consisting of hydroxyl, halogen, a polyether radical with up to 60 carbon atoms, and/or two radicals $R^1$ from different siloxy moieties form a group $R^3$ which is selected from divalent hydrocarbon radicals which have up to 30 carbon atoms, and may contain optionally one or more groups selected from —O—, —NH—, —C(O)—, —C(S)—, tertiary amino groups

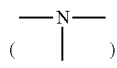

and quaternary ammonium groups

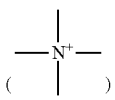

and wherein $R^3$ may optionally be substituted by one or more hydroxyl groups or halogen atoms, with the proviso that $R^3$ is bound to the silicon atoms via a carbon atom, and/or $R^{F2}$ is selected from hydrocarbon radicals which have up to 100 carbon atoms and may contain one or more groups selected from —O—, —S—, —$NR^2$—, in which $R^2$ is selected from the group consisting of hydrogen, a monovalent, straight-chain, cyclic or branched, saturated, unsaturated or aromatic hydrocarbon radical which has up to 60 carbon atoms and which may contain one or more groups selected from —O—, —S—, —NH—, —C(O)— and —C(S)—, and which may be substituted by one or two hydroxyl groups, and which may optionally be substituted by one or more substituents selected from the group consisting of a hydroxyl group, an optionally substituted heterocyclic group optionally containing one or more nitrogen atoms, amino, alkylamino, dialkylamino, polyether radicals and polyetherester radicals, where, when a plurality of —$NR^2$— groups is present, they may be the same or different, and with the proviso that $R^{F2}$ contains at least one substituent group that comprises a functional group F2.

12. The aqueous composition according to claim 1, wherein $R^{F1}$ has the structure:

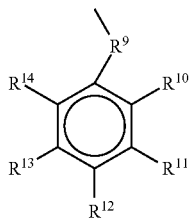

wherein
$R^9$ is selected from $R^3$ which is selected from divalent hydrocarbon radicals which have up to 30 carbon atoms, and may contain optionally one or more groups selected from —O—, —NH—, —C(O)—, —C(S)—, tertiary amino groups

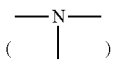

and quaternary ammonium groups

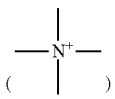

and wherein $R^3$ may optionally be substituted by one or more hydroxyl groups or halogen atoms, with the proviso that $R^3$ is bound to the silicon atoms via a carbon atom, and wherein $R^3$ optionally substituted by nitrogen containing groups, such as —$NH_2$, —$NHR^2$, —$N(R^2)_2$, wherein $R^2$ is selected from the group consisting of hydrogen, a monovalent, straight-chain, cyclic or branched, saturated, unsaturated or aromatic hydrocarbon radical which has up to 60 carbon atoms and which may contain one or more groups selected from —O—, —S—, —NH—, —C(O)— and —C(S)—, and which may be substituted by one or two hydroxyl groups, and which may optionally be substituted by one or more substituents selected from the group consisting of a hydroxyl group, an optionally substituted heterocyclic group optionally containing one or more nitrogen atoms, amino, alkylamino, dialkylamino, polyether radicals and polyetherester radicals, where, when a plurality of —$NR^2$— groups is present, they may be the same or different, and $R^{10}$, $R^{11}$, $R^{12}$, $R^{13}$, $R^{14}$ are the same or different from each other and are selected from hydroxyl and $R^2$, as defined above, with the proviso that 2 to 3 groups $R^{10}$ to $R^{14}$ are hydroxyl (—OH).

13. The aqueous composition according to claim 1, wherein the polyorganosiloxanes A) are selected from the formulas:

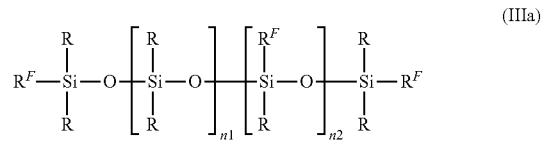

(IIIa)

wherein
R is $R^1$, and $R^F$ is selected from $R^{F1}$ as defined and $R^{F2}$ is different from $R^1$ and $R^{F1}$, and is bound to the silicon atoms by a carbon atom and which comprises at least one functional group F2, selected from the group consisting of:
alkoxy silyl group,
amino group, or azetidine group,
ammonium group, or azetidinium group,
phosphonium group,
epoxy group,
carbonate group,
urethane group,
isocyanate group, or blocked isocyanate group,
urea group,
amido group, or carbamoyl group,
aldehyde group,
methylol group,
acetale or half acetale group,
Schiff-Base or enamine group,
zwitterionic group,
carboxylic acid or carboxylate group,
sulfonic acid or sulfonate group,
sulfuric acid half ester or sulfate group,
phosphoric acid ester or phosphate group,
phosphonic acid ester or phosphonate group,
phosphorous acid ester or phosphite group,
xanthogenate/xanthogenate ester group,
thiosulfato group,
a monohydroxy-substituted aromatic group,
mercapto group,
saccharide group,
polyether group with up to 60 carbon atoms,
thio ester,
thio ether group, and
combinations of said functional groups,
with the proviso that at least one $R^{F1}$ is $R^{F2}$, and the sum of the average numbers n1+n2 is 0 to 28,

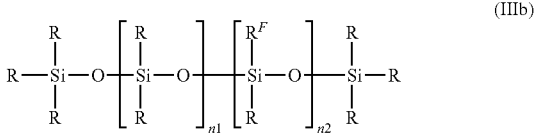

(IIIb)

wherein
R is $R^1$, and $R^F$ is selected from $R^{F1}$ and $R^{F2}$, each as defined, with the proviso that at least one $R^F$ is $R^{F1}$, and the sum of the average numbers n1+n2 is 1 to 28, with n2≥1, and

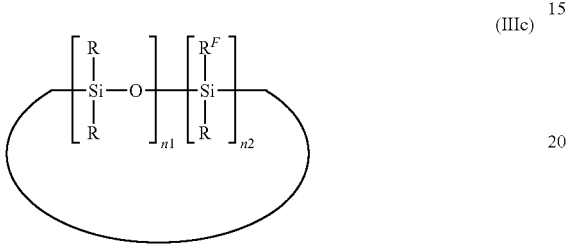

(IIIc)

wherein
R is $R^1$, and $R^F$ is selected from $R^{F1}$ and $R^{F2}$, each as defined above, with the proviso that at least one $R^F$ is $R^{F1}$, and wherein the sum of the average numbers n1+n2 is 3 to 7 with n2≥1, and
wherein in the above polysiloxane formulas the siloxy units having indices n1 and n2 can be arranged in any order including regular alternatingly arranged units, periodically arranged units, statistically arranged units or blockwise arranged units.

14. The aqueous composition according to claim 1, wherein the surfactant B) is selected from cationic surfactants B1) selected from quaternary ammonium compounds or amino compounds having up to 50 carbon atoms, each containing linear or branched, optionally substituted alkyl groups with up to 20 carbon atoms which optionally contain further heteroatoms, such as nitrogen, oxygen, including ester quats having at least one quaternary ammonium group and at least one ester group or anionic surfactants B2) selected from carboxylates, sulfates, sulfonates, phosphates and phosphonates having up to 50 carbon atoms, each containing linear or branched, optionally substituted alkyl groups with up to 20 carbon atoms which optionally contain further heteroatoms, such as nitrogen or oxygen.

15. The aqueous composition according to claim 1, comprising one or more additional additives, selected from the group consisting of:

C) organic diluents or solvents,
D) proteins,
E) preservatives,
F) skin protecting ingredients,
G) oxidizing agents,
H) reducing agents,
I) tannins,
J) metal salts, and
K) further auxiliaries selected from pH adjusting agents, thickeners, lipids, amino acids, sugars, fragrances, sunscreen agents, vitamins, pearlescent agents, gelling agents, trace elements, sequestering agents, antioxidants, humectants, anti-hair loss agents, antidandruff agents, propellants, ceramides, polymers, fillers, nacres, colorants, and mixtures thereof,
with the proviso that oxidizing agents and reducing agents are not present simultaneously in a given composition.

16. The aqueous composition according to claim 1, further comprising at least one metal salt L) as a hair strengthening additive which is a metal compound of the general formula:

$$Me(A^-)_n$$

wherein Me is the cation of a metal of valence n, n is 2 or 3, each $A^-$ independently is (i) the anion of an oxidized carbohydrate of the formula $^-O-C(O)-R^4$ in which $R^4$ is the residue of the same or different carbohydrate, or (ii) an anion derived from an inorganic or organic acid.

17. The aqueous composition according to claim 1, comprising the following components:

| | Ingredient | Weight-% |
|---|---|---|
| A) | polyorganosiloxane | 0.05 to 30 |
| B) | Surfactant B) selected from B1) and B2) | 0.05 to 15 |
| C) | diluents/solvents | 0 to 95 |
| D) | protein, preferred keratin | 0 to 15 |
| E) | emollients/fatty substance | 0 to 15 |
| F) | preservatives | 0 to 5 |
| G) | skin protecting ingredients | 0 to 15 |
| H) | conditioning agents | 0 to 15 |
| I) | oxidizing agents | 0 to 15 |
| J) | reducing agents | 0 to 15 |
| K) | tannins | 0 to 15 |
| L) | water soluble Fe and/or Zn salt | 0 to 15 |
| M) | further auxiliaries | 0 to 15. |

18. A hair treatment composition comprising the aqueous composition according to claim 1.

\* \* \* \* \*